US011141078B2

(12) United States Patent
Satoh et al.

(10) Patent No.: US 11,141,078 B2
(45) Date of Patent: Oct. 12, 2021

(54) MAGNETIC RESONANCE IMAGING DEVICE, MAGNETIC RESONANCE IMAGING METHOD AND SUSCEPTIBILITY CALCULATION PROGRAM

(71) Applicant: Hitachi, Ltd., Tokyo (JP)

(72) Inventors: Ryota Satoh, Tokyo (JP); Toru Shirai, Tokyo (JP); Yo Taniguchi, Tokyo (JP); Yoshitaka Bito, Tokyo (JP); Hisaaki Ochi, Tokyo (JP); Yoshihisa Sotome, Tokyo (JP)

(73) Assignee: HITACHI, LTD., Tokyo (JP)

( * ) Notice: Subject to any disclaimer, the term of this patent is extended or adjusted under 35 U.S.C. 154(b) by 417 days.

(21) Appl. No.: 16/097,284

(22) PCT Filed: May 24, 2017

(86) PCT No.: PCT/JP2017/019381
§ 371 (c)(1),
(2) Date: Oct. 29, 2018

(87) PCT Pub. No.: WO2017/204251
PCT Pub. Date: Nov. 30, 2017

(65) Prior Publication Data
US 2019/0076049 A1  Mar. 14, 2019

(30) Foreign Application Priority Data

May 25, 2016 (JP) .............................. JP2016-104358

(51) Int. Cl.
*A61B 5/05* (2021.01)
*A61B 5/055* (2006.01)
(Continued)

(52) U.S. Cl.
CPC ............ *A61B 5/055* (2013.01); *G01R 33/243* (2013.01); *G01R 33/4828* (2013.01);
(Continued)

(58) Field of Classification Search
None
See application file for complete search history.

(56) References Cited

U.S. PATENT DOCUMENTS

2004/0010191 A1* 1/2004 Yatsui .................. A61B 5/4872
600/410
2014/0142417 A1  5/2014 Reeder et al.
(Continued)

OTHER PUBLICATIONS

International Preliminary Report on Patentability received in corresponding International Application No. PCT/JP2017/019381 dated Dec. 6, 2018.
Sun H et al., Quantitative susceptibility mapping using a superposed dipole inversion method: Application to intracranial hemorrhage, Magnetic Resonance in Medicine, 2015, pp. 1-11.
(Continued)

*Primary Examiner* — Joel F Brutus
(74) *Attorney, Agent, or Firm* — Mattingly & Malur, PC

(57) ABSTRACT

Accuracy degradation due to a signal loss is reduced, and susceptibility is calculated with high accuracy where, by using an MRI, at least one echo is acquired where spatial magnetic field inhomogeneity is reflected, and a complex image is calculated from the acquired echo. Three masks are calculated from the calculated complex image; a low-signal region mask representing a low signal region, a first high-signal region mask representing a high signal and high fat content region, and a second high-signal region mask representing a high signal and low fat content region. In calculating a susceptibility image from a frequency image or a magnetic field image generated from the complex image, the susceptibility image is obtained under the constraint that a region defined by the low-signal region is set as a background and the susceptibility of the region defined by the second high-signal region mask is set to a specific value.

15 Claims, 19 Drawing Sheets

(51) Int. Cl.
*G01R 33/24* (2006.01)
*G01R 33/48* (2006.01)
*G01R 33/56* (2006.01)
*G01R 33/565* (2006.01)
*A61B 5/00* (2006.01)

(52) U.S. Cl.
CPC .......... *G01R 33/56* (2013.01); *A61B 5/0042* (2013.01); *A61B 2576/026* (2013.01); *G01R 33/56536* (2013.01); *G06T 2207/10088* (2013.01)

(56) References Cited

U.S. PATENT DOCUMENTS

2015/0002148 A1  1/2015  Liu
2015/0168525 A1* 6/2015  Sato ................. G01R 33/5608
                                              324/318

OTHER PUBLICATIONS

Sharma S et al., Quantitative susceptibility mapping in the abdomen as an imaging biomarker of hepatic iron overload, Magnetic Resonance in Medicine, vol. 74, Issue 3, 2014.
Rochefort L et al., Quantitative susceptibility map reconstruction from MR phase data using baysian regularization: Validation and application to brain imaging, Magnetic Resonance in Medicine, vol. 63, Issue 1. 2010. pp. 194-206.
Wei, et al., Imaging Magnetic Susceptibility of the Human Knee Joint At 3 and 7 Tesla, Proceedings of International Society for Magnetic Resonance in Medicine, vol. 23, 2015, pp. 0288.
Khalidov, I.et al., Susceptibility mapping: computation of the field map using water-fat separation at 7T, Proceedings pf International Society for magnetic Resonance in Medicine, vol. 19, 2011, pp. 4475.
International Search Report of PCT/JP2017/019381 dated Aug. 15, 2017.

* cited by examiner

MAGNETIC RESONANCE IMAGING DEVICE, MAGNETIC RESONANCE IMAGING METHOD AND SUSCEPTIBILITY CALCULATION PROGRAM

TECHNICAL FIELD

The present invention relates to a magnetic resonance imaging (MRI) technique. More particularly, it relates to an image processing technique on a reconstructed image.

BACKGROUND ART

A magnetic resonance imaging apparatus (hereinafter, referred to as "MRI apparatus") is medical diagnostic imaging equipment that applies an RF magnetic field and a gradient magnetic field to a subject placed in a static magnetic field, measures signals generated from the subject in response to nuclear magnetic resonance, and create an image.

The MRI apparatus allows obtainment of an image (an image where a phase is used as a pixel value: phase image) on which magnetic field variations are reflected, due to causes such as static magnetic field inhomogeneity and a susceptibility difference between living tissues, in addition to an image (an image where an absolute value is used as the pixel value) on which the density of protons (hydrogen nucleus) and relaxation time (T1, T2) are reflected.

In recent years, there are suggested various methods including a quantitative susceptibility mapping (QSM) method, which utilizes a feature that a susceptibility difference between tissues is reflected on the phase image, and a susceptibility distribution in a living body can be estimated from this phase image (e.g., Non Patent Documents 1 and 2). The susceptibility distribution (hereinafter, referred to as susceptibility image) estimated by the QSM method allows calculation of the concentration of iron in basal ganglia and oxygen extraction fraction of cerebral veins. Therefore, the QSM method is expected to be useful for early diagnostic detection of brain diseases including neurodegenerative disease and cerebrovascular disease. In addition, it is studied to apply the QSM method to the body core. As representative examples, the QSM method can be applied to detection of breast calcifications and to estimation of liver iron concentration, for instance (Non Patent Document 3). It is also expected to apply the QSM method to detection of hypoxic regions and calcifications in a prostate gland.

PRIOR ART DOCUMENT

Non Patent Document

Non Patent Document 1
Sun H, et al., Quantitative susceptibility mapping using a superposed dipole inversion method: Application to intracranial hemorrhage, Magnetic Resonance in Medicine Non Patent Document 2
Sharma S, et al., Quantitative susceptibility mapping in the abdomen as an imaging biomarker of hepatic iron overload, Magnetic Resonance in Medicine, vol. 74, No. 3, pp. 673-683 (2015)

Non Patent Document 3
Rochefort L, et al., Quantitative susceptibility map reconstruction from MR phase data using baysian regularization: Validation and application to brain imaging, Magnetic Resonance in Medicine, vol. 63, No. 1, pp. 194-206 (2010)

DISCLOSURE OF THE INVENTION

Problems to be Solved by the Invention

The prostate gland is an organ peculiar to men, located at the lower abdomen and adjacent to subcutaneous fat, such as buttocks. Such subcutaneous fat may cause reduction in accuracy in calculating a prostate susceptibility image. One of the causes that may reduce the calculation accuracy in the QSM method is a loss of MRI signals in an edge region of target tissue. Accuracy reduction due to the loss of signals is likely to occur in the subcutaneous fat near the prostate, because there are found following regions around the subcutaneous fat, for example, a region where signals are undetectable or a low-signal region, such as outside-body parts and bones. In addition, the reduction in accuracy in calculating the susceptibility may propagate to an adjacent region, and thus, the accuracy in calculation is also reduced in a water region such as the prostate gland that is adjacent to the subcutaneous fat.

Non Patent Document 1 discloses a method that the susceptibility of intracranial hemorrhage (ICH) and that of the other region are calculated separately, and then both results are combined. Non Patent Document 2 discloses a method that smooths a fat region strongly to obtain the liver susceptibility. In any of the methods as described above, the susceptibility is calculated under the constraint that pixel values in a susceptibility image are smoothed. Smoothing allows reduction of noise and artifacts, however, it is considered to be difficult to reduce the accuracy degradation caused by the loss of signals. Non Patent Document 3 discloses a method that a background field is removed, assuming a region outside the brain as the background, and thereafter, the susceptibility inside the brain is calculated under the constraint that the susceptibility in the region outside the brain is zero. In this method, the constraint is placed on the susceptibility in the region outside the brain, enabling highly accurate calculation of a susceptibility image. However, when this method is applied to the calculation of the subcutaneous fat, the background field removal is performed, assuming a water region, which is a high-signal region, as the background. Therefore, the susceptibility cannot be calculated with the use of magnetic field information of the water region, and thus accuracy is deteriorated.

The present invention has been made in view of the aforementioned situations, and an object of the present invention is to reduce the accuracy degradation due to the signal loss, and to calculate the susceptibility with high accuracy.

Means for Solving the Problems

According to the present invention, a nuclear magnetic resonance signal (echo) on which spatial magnetic field inhomogeneity is reflected is measured, and a complex image is calculated from the echo, thereby obtaining a magnetic field image. Then, an absolute value image is calculated from the complex image, and based on the absolute value image, three or more masks are calculated, such as a low-signal region mask representing a low-signal region, and a plurality of masks (e.g., a first high-signal region mask and a second high-signal region mask) that represent high-signal regions, being divided according to a predetermined threshold of a discriminant image. Then, using the plurality of masks including the low-signal region mask, the susceptibility is calculated as to each of the plurality of regions that are high-signal regions, having different magnetic susceptibilities. Then, a susceptibility image is calculated for the susceptibility of one region, under the constraint that the susceptibility of the other region is set to a predetermined specific value (a specific value constraint).

The MRI apparatus of the present invention includes a static magnetic field magnet, a magnetic field generator configured to apply a gradient magnetic field and an RF magnetic field to space formed by the static magnetic field magnet, a receiver configured to receive a nuclear magnetic resonance signal generated from a subject placed in the space, and a computer configured to perform computations on the nuclear magnetic resonance signal, and the computer is provided with a measurement unit configured to control operations of the magnetic field generator and of the receiver, and to measure the nuclear magnetic resonance signal including effects of magnetic field inhomogeneity, and an image reconstructor configured to perform image reconstruction by using the nuclear magnetic resonance signal, so as to create a complex image, and an image converter configured to calculate a susceptibility image of the subject, by using the complex image.

The image converter includes a magnetic field calculator configured to calculate a magnetic field reflected image from the complex image, a mask calculator configured to use the image created by the image reconstructor to calculate a low-signal region mask associated with a low-signal region, and a plurality of region masks associated with a plurality of regions in a high-signal region, and a susceptibility calculator configured to use the magnetic field reflected image calculated by the magnetic field calculator, the low-signal region mask and the plurality of region masks calculated by the mask calculator, so as to calculate susceptibility as to each of the plurality of regions, and the susceptibility calculator calculates the susceptibility of the region different from a specific region, under a first constraint that the low-signal region is set as a background, and a second constraint that the susceptibility of the specific region among the plurality of the regions is set to a specific value. The magnetic field reflected image is an image having a pixel value representing a frequency or a magnetic field, and spatial magnetic field inhomogeneity is reflected thereon.

Advantage of the Invention

The accuracy degradation due to the loss of signals can be reduced, and this allows calculation of the susceptibility with a high degree of accuracy.

BEST MODE FOR CARRYING OUT THE INVENTION

Figure 1:
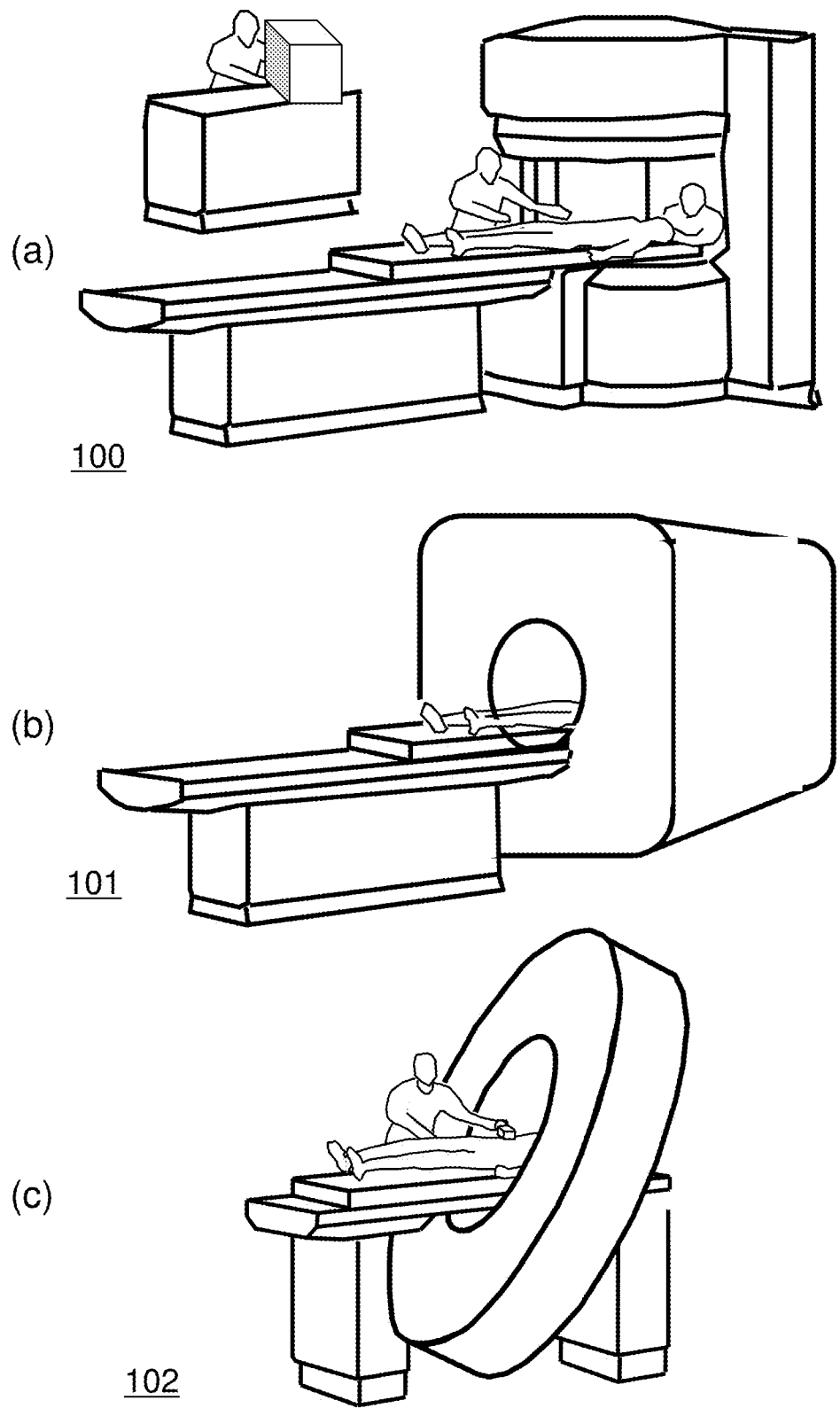
FIG. 1(a) is an external view of a vertical magnetic resonance imaging apparatus.
FIG. 1(b) is an external view of a horizontal magnetic resonance imaging apparatus.
FIG. 1(c) is an external view of the magnetic resonance imaging apparatus with enhanced sense of space.

Embodiments to which the present invention is applied will now be described, with reference to the accompanying drawings. Hereinafter, in all the figures illustrating the embodiments of the present invention, elements with an identical function are labeled with the same reference numeral, and they will not be redundantly explained. It should be noted that the following description is not intended to limit the scope of the present invention.

There will now be described an overview of an MRI apparatus to which the present invention is applied. FIG. 1 is an external view of the MRI apparatus. FIG. 1(a) illustrates the MRI apparatus (vertical magnetic field MRI apparatus) 100 of a hamburger-type (open-type) vertical magnetic field system in which the magnets are separated vertically so as to enhance a sense of openness. FIG. 1(b) illustrates the MRI apparatus of a horizontal magnetic field type (horizontal magnetic field MRI apparatus) 101 that uses a tunnel-type magnet for generating a static magnetic field by a solenoid coil. FIG. 1(c) illustrates the MRI apparatus 102 using the same tunnel-type magnet as FIG. 1(b), the magnet having a reduced depth and put in a slanting position, thereby enhancing the sense of openness. It should be noted that each mode of the MRI apparatus as shown in FIG. 1 is an example of the vertical magnetic field system or the horizontal magnetic field system, and they are not limited to those examples shown here. The horizontal-field MRI apparatus 101 will now be described as a representative example in the following.

Figure 2:
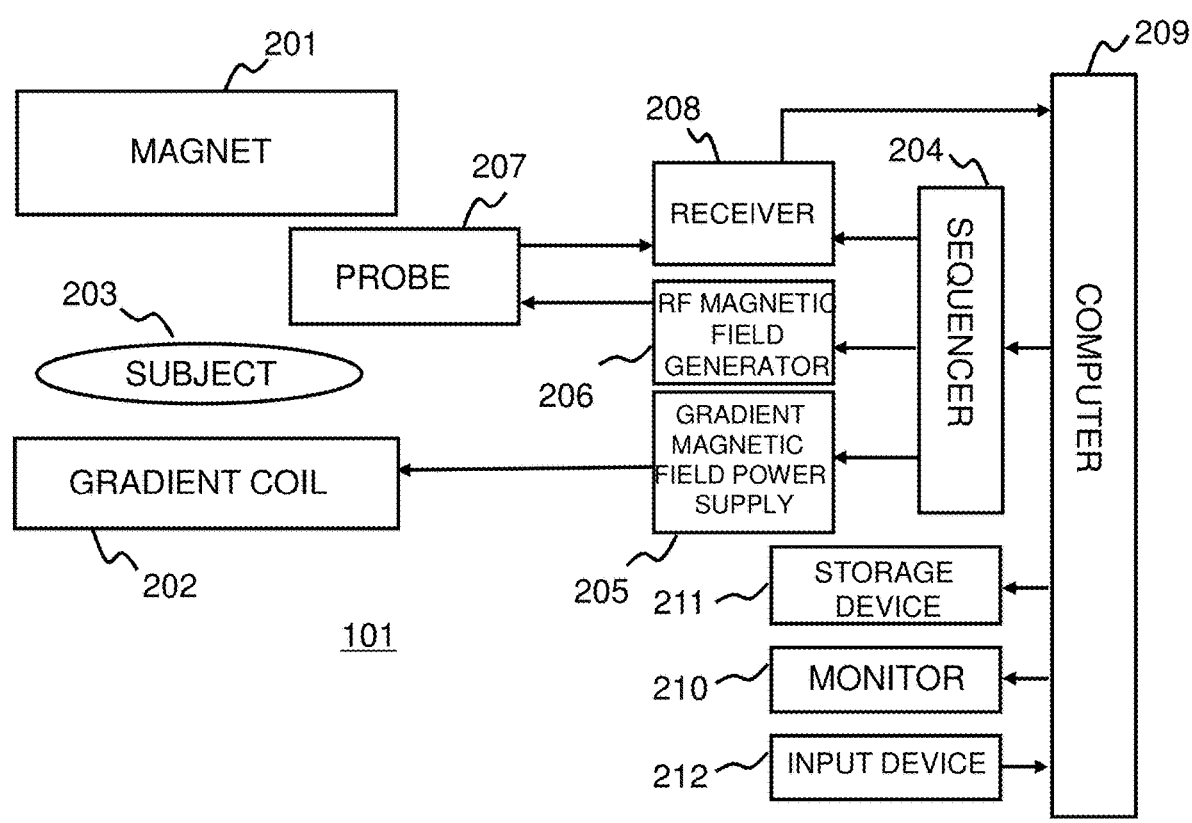
FIG. 2 is a block diagram showing a schematic configuration of an MRI apparatus.

FIG. 2 is a block diagram showing a schematic configuration of the MRI apparatus 101. This MRI apparatus 101 is provided with a magnet 201 for generating a static magnetic field in a direction parallel to the subject, a gradient coil 202 for generating a gradient magnetic field, a sequencer 204, a gradient magnetic field power supply 205, an RF magnetic field generator 206, a probe 207 for emitting an RF magnetic field and for detecting a nuclear magnetic resonance signal (echo), a receiver 208, a computer 209, a monitor 210, and a storage device 211. The subject (e.g., a living body) 203 is placed on a table or the like, and disposed in the static magnetic field space generated by the magnet 201.

The sequencer 204 transfers instructions to the gradient magnetic field power supply 205 and to the RF magnetic field generator 206, thereby allowing generation of the gradient magnetic field and the RF magnetic field, respectively. Thus generated RF magnetic field is applied to the subject 203 via the probe 207. The echoes generated from the subject 203 are received by the probe 207, and are subjected to detection by the receiver 208.

The sequencer 204 sets a nuclear magnetic resonance frequency (detection reference frequency f0) that is a reference of the detection. Signals being detected are transferred to the computer 209, and those signals are subjected to signal processing such as an image reconstruction. The monitor 210 displays the result thereof. If necessary, the storage device 211 may store the detected signals, measurement conditions, image information after the signal processing, and the like. The sequencer 204 performs control so that each unit operates at predetermined timing and strength. Programs include, in particular, a program referred to as a pulse sequence that describes the timing and strength of the RF magnetic field, the gradient magnetic field, and the signal reception.

Various pulse sequences are known depending on the purposes. Since the present embodiment aims at calculating susceptibility on the basis of spatial magnetic field variations obtained from a phase image, there is employed a pulse sequence for acquiring at least one echo that reflects inhomogeneity of spatial distribution of magnetic field strength, that is, an echo that produces phase shift of each spin due to the spatial magnetic field variation. By way of example, GrE (Gradient Echo) type pulse sequence may be employed as such pulse sequence as described above. The GrE type pulse sequence may include, for example, an RSSG (RF-spoiled-Steady-state Acquisition with Rewound Gradient-Echo) sequence.

The computer 209 of the present embodiment instructs the sequencer 204 to measure echoes according to the measurement parameters set via the input device 212 (or set in advance) and the pulse sequence, measures the echoes, places thus obtained echoes in k-space, performs computation on the echoes placed in k-space to calculate a susceptibility image, and displays thus obtained image on the monitor 210. If required, an ROI (Region of Interest) is set on the image, and the computer calculates statistical values of pixels within the ROI.

A CPU of the computer 209 loads programs held in the storage device 211 into the memory and executes those programs, whereby those functions as described above are implemented by the computer 209. A part or all of the functions of the computer 209 may be implemented by hardware such as ASIC (Application Specific Integrated Circuit) and FPGA (Field Programmable Gate Array).

Specifically, the programs of the present embodiment includes, a measurement program for executing a predetermined pulse sequence, an image reconstruction program for creating a complex image and an absolute value image, by using measured echoes, a mask calculation program for calculating at least three different region masks by using the absolute value image, a magnetic field calculation program for calculating a frequency image or a magnetic field image from the complex image, and a susceptibility calculation program for calculating a susceptibility image, using the frequency image or the magnetic field image, and the different region masks at least three.

Those programs and functions implemented by executing the programs will be described in the following embodiments.

First Embodiment

In the present embodiment, a susceptibility distribution is calculated with respect to each of a water region (a region where water proton signals are dominant) and a fat region (a region where fat proton signals are dominant), and the calculated susceptibility distributions are combined. In calculating the susceptibility distribution, there are given a constraint that the susceptibility should be a specific value in a specific region, in addition to a constraint of smoothing. By way of example, the specific region is the water region, and the specific value is zero.

Figure 3:
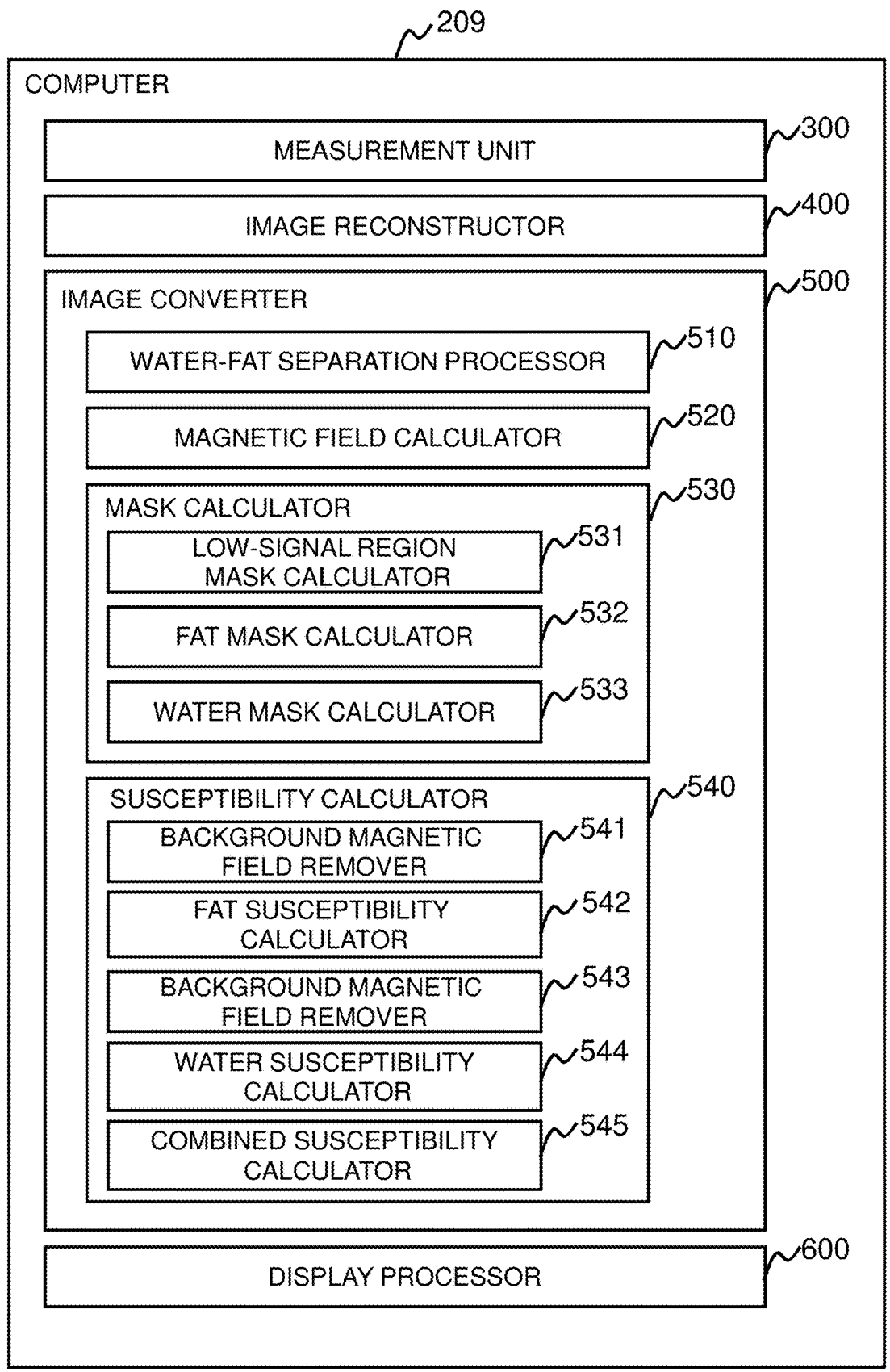
FIG. 3 is a functional block diagram of a computer according to a first embodiment.

FIG. 3 is a functional block diagram of the computer 209 that performs the processing above according to the present embodiment. As illustrated, the computer 209 includes a measurement unit 300, an image reconstructor 400, an image converter 500, and a display processor 600, as primary components. The image converter 500 includes a water-fat separation processor 510, a magnetic field calculator 520, a mask calculator 530, and a susceptibility calculator 540. Details of the mask calculator 530 and the susceptibility calculator 540 will be described later.

Figure 4:
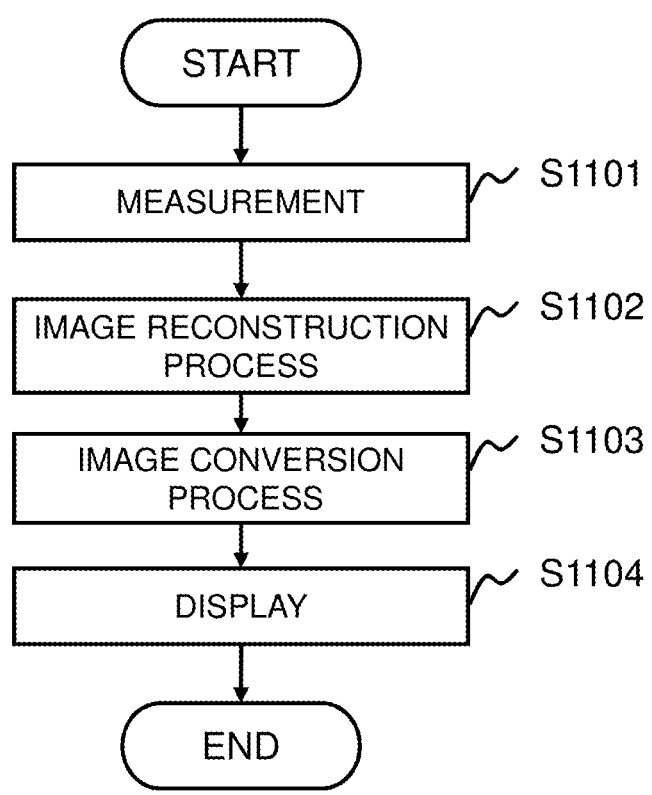
FIG. 4 is a flowchart of an imaging process according to the first embodiment.

There will now be described details of the imaging processing according to the components above, along the processing flowchart as shown in FIG. 4.

[Measurement (S1101)]

Upon accepting an instruction to start imaging with the setting of various measurement parameters, the measurement unit 300 performs measurements (S1101). In this example, the measurement unit 300 provides an instruction to the sequencer 204, according to a predetermined pulse sequence, acquires echo signals, and places the echo signals in k-space. As described above, the sequencer 204 transmits commands to the gradient magnetic field power supply 205 and to the RF magnetic field generator 206, allowing generation of a gradient magnetic field and an RF magnetic field, respectively. Then, the echoes are received by the probe 207 and detected by the receiver 208, and then received in the form of complex signals.

Figure 5:
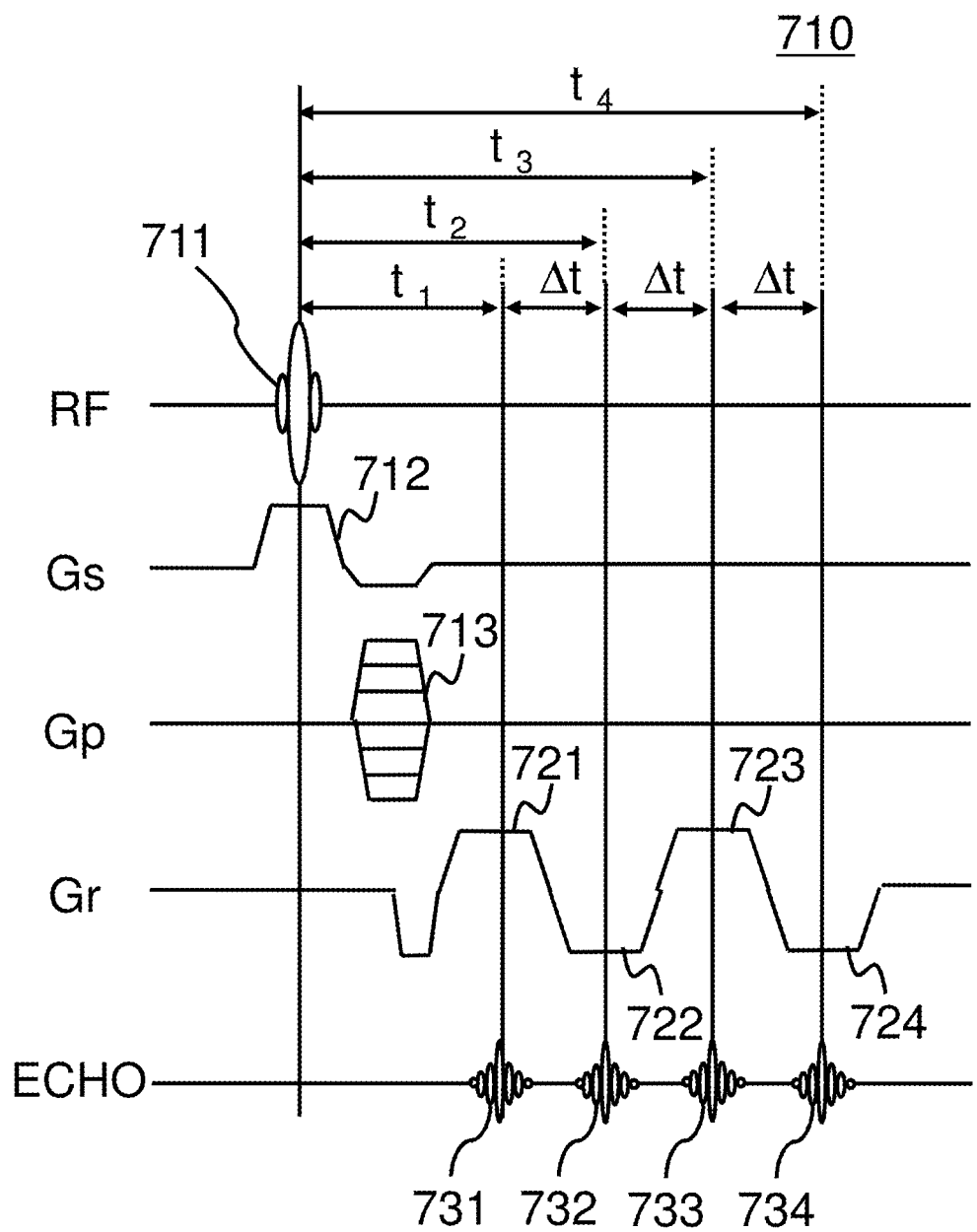
FIG. 5 illustrates one example of a gradient echo-type pulse sequence according to the first embodiment.

In the present embodiment, for example, the GrE-type pulse sequence is employed as the pulse sequence, which measures at least one echo where a phase shift is produced as to each spin, in association with spatial magnetic field inhomogeneity. FIG. 5 illustrates one example of the measurement sequence that is executed in the measurement performed by the measurement unit 300 in step S1101. In FIG. 5, RF, Gs, Gp, and Gr represent application timing, respectively, of an RF pulse, a slice selective gradient magnetic field, a phase encoding gradient magnetic field, and a readout gradient magnetic field. The echo represents a timing of acquiring an echo signal.

In the measurement sequence 710, the echo signal is measured according to the following procedures in every repetition time TR. In the present embodiment, two or more echoes are acquired within one TR, in order to calculate a water image and a fat image using a frequency difference between water and fat. In this example here, there is illustrated the case where echo signals are acquired at four different echo times. Here, $t_1$ represents the first echo time and $\Delta t$ represents time interval until a subsequent echo (echo interval).

Firstly, an RF pulse 711 is applied, and a hydrogen nucleus spin of the subject 203 is excited. At this time, the slice selective gradient magnetic field (Gs) 712 is applied simultaneously with the RF pulse 711, so as to select a specific slice of the subject 203. Then, the phase encoding gradient magnetic field (Gp) 713 is applied to perform phase-encoding on the echo signal. Thereafter, the readout gradient magnetic field (Gr) 721 is applied after a lapse of $t_1$ from the application of the first RF pulse 711, and an echo signal (a first echo signal) 731 is measured. Furthermore, at the time $t_2$ after a lapse of $\Delta t$ from the measurement of the first echo signal 731, the readout gradient magnetic field (Gr) 722 with the reversed polarity is applied, and an echo signal (a second echo signal) 732 is measured. Similarly, at the time $t_3$ after a lapse of $\Delta t$ from the measurement of the second echo signal 732, the readout gradient magnetic field (Gr) 723 with the reversed polarity is applied, and an echo signal (a third echo signal) 733 is measured. Furthermore, at the time $t_4$ after a lapse of $\Delta t$ from the measurement of the third echo signal 733, the readout gradient magnetic field (Gr) 724 with the reversed polarity is applied, and an echo signal (a fourth echo signal) 734 is measured.

The echo time $t_1$ and the echo interval $\Delta t$ are provided, in a manner that at least one of the echo times $t_1$, $t_2$, $t_3$, and $t_4$ for measuring the first echo signal 731, the second echo signal 732, the third echo signal 733, and the fourth echo signal 734, respectively, should become the point of time when a phase difference between water and fat is not zero. Assuming the time when water and fat become in phase as $t_{In}$, $t_{In}$ is expressed by $m/f_{wf}$ where a frequency difference between water and fat is $f_{wf}$ and m is integer.

In the measurement sequence 710, there are selected the echo times $t_1$, $t_2$, $t_3$, and $t_4$, or the echo time $t_1$ and the echo interval $\Delta t$, satisfying the aforementioned conditions. In the present embodiment, a user sets the echo time, the echo interval, and the echo acquisition count, via the input device 212. Alternatively, those are preset.

The measurement unit 300 iterates application of the RF pulse 711 to a predetermined imaging area of the subject 203, and measurement of the echo signals 721, 732, 733, and 734, from the imaging area, for a predetermined number of times, while varying strength of the phase encoding gradient magnetic field 713 according to the measurement sequence 710. The number of repetitions may be 128, 256, or other numbers, for example. Accordingly, the required number of echo signals for reconstructing an image of the imaging area is acquired repeatedly. One original image (a first original image) is formed on the basis of the first echo signals 731 corresponding to the number of repetitions. With the second signals 732, the third echo signals 733, and the fourth echo signals 734, each corresponding to the number of repetitions, there are formed the second original image, the third original image, and the fourth original image, respectively. Those original images are stored in the storage device and used as original images for computations in order to obtain a water image and a fat image as described in the following.

It is to be noted that the number of different echo times, that is, the number of original images is not limited to four, and any number is applicable. Further, non-Cartesian imaging may be employed, such as radial scanning that acquires data rotationally in space.

[Image Reconstruction (S1102)]

After the measurement, the image reconstructor 400 performs image reconstruction for reconstructing an image from the echo signals measured at respective echo times $t_1$, $t_2$, $t_3$, and $t_4$ (step S1102). Here, each of the echo signals is arranged in k-space, and Fourier transform is applied to those echo signals. Accordingly, the original image $I_1$ (the first original image), the original image $I_2$ (the second original image), the original image $I_3$ (the third original image), and the original image $I_4$ (the fourth original image) of the echo times $t_1$, $t_2$, $t_3$, and $t_4$ are calculated, respectively. Each of the original images is a complex image where each pixel value is a complex number.

[Image Conversion (S1103)]

The image converter 500 performs various image conversion processes on thus obtained complex images, which will be described below (step S1103). In the present embodiment, the image converter 500 includes a water-fat separation processor 510 configured to convert complex images obtained by the image reconstructor 400 into a water image, a fat image, and a frequency image, a magnetic field calculator 520 configured to convert the frequency image calculated in the water-fat separation processor 510 into a magnetic field image, a mask calculator 530 configured to calculate three masks; a low-signal region mask, a fat mask, and a water mask, from the complex images, the water image, and the fat image, and a susceptibility calculator 540 configured to calculate a susceptibility image from the magnetic field image and the three masks. Details of the image conversion process according to the present embodiment will be described later.

[Display (S1104)]

The display processor 600 displays thus obtained susceptibility image on the monitor 210, in the form of a gray-scale image (step S1104). The susceptibility image may be displayed by integrating a plurality of spatially continuous image information items, using methods such as maximum intensity projection and minimum intensity projection. In addition, an image processing is applied to the susceptibility image, thereby creating an image with contrast different from the susceptibility image, and displaying thus created image on the monitor 210. By way of example, a weighting mask that weights a susceptibility difference between tissues is created from the susceptibility image, and an absolute value image is multiplied by the weighting mask, so as to obtain and display a susceptibility difference weighted image. In the susceptibility difference weighted image, the process for weighting the susceptibility difference may cause a loss of susceptibility information of the tissue, but the tissue with high susceptibility becomes more noticeable by contrast with the other tissue. Therefore, the tissue with high susceptibility can be depicted clearly.

Next, there will be described in detail, a processing of the image converter 500 (S1103) according to the present embodiment. Prior to describing the processing of the present embodiment (S1103), firstly, general susceptibility calculation methods will be described briefly.

In general susceptibility calculation methods, initially a background removal process is performed where global magnetic field change caused by susceptibility differences, for instance, between outside and inside of the body are eliminated, and then a local magnetic field caused by a susceptibility difference between living tissues is calculated. Thereafter, on the basis of a relational expression between magnetic field changes and a susceptibility distribution, the susceptibility is calculated.

As a representative example of the background field removing method, there are methods such as SHARP (sophisticated harmonic artifact reduction for phase data) method and PDF (projection onto dipole field) method. In the SHARP method and PDF method, the region is divided into two regions; a region of interest (here, a region as to which the susceptibility is to be calculated) and a background region, and then, the background removal process is performed.

After the background removal process is performed, the following relational expression (formula 1) between the relative magnetic field change δ and the susceptibility distribution χ is used to calculate the susceptibility:

[Formula 1]

$$\delta(r) = \frac{1}{4\pi} \int \chi(r') \frac{3\cos^2\alpha - 1}{|r' - r|} dr'^3 \qquad (1)$$
$$= d(r) \otimes \chi(r)$$

where α is angle formed by the vector (r'−r) and a direction of the static magnetic field, and d(r) is a point-dipole magnetic field. A position vector in association with a pixel coordinate is represented by r.

As indicated by the formula 1, the magnetic field distribution δ(r) is expressed by convolution integral of the susceptibility distribution χ(r) and the point-dipole magnetic field d(r). Therefore, when Fourier transform is applied to both sides of the formula 1, the formula 1 is transformed to the formula 2:

[Formula 2]

$$\Delta(k) = \left(\frac{1}{3} - \frac{k_z^2}{k_x^2 + k_y^2 + k_z^2}\right) \cdot X(k) \qquad (2)$$
$$= D(k) \cdot X(k)$$

where k=(kx, ky, kz) are position vectors in k-space, and Δ(k), X(k), and D(k) are Fourier components, respectively of the magnetic field distribution δ(r), the susceptibility distribution χ(r), and the point-dipole magnetic field d(r).

As indicated in the formula 2, the Fourier component X(k) of the susceptibility distribution is obtained by dividing the Fourier components Δ(k) by the Fourier components D(k) of the point-dipole magnetic field. However, according to the formula 2, the reciprocal of D(k) diverges near the region D(k)=0, and thus X(k) cannot be calculated directly.

This region where D(k)=0 is referred to as a magic angle, and this forms a reverse bi-cone region that has an apex angle approximately twice as large as 54.7° with respect to the magnetic field direction. With this magic angle, the QSM method that assumes the susceptibility distribution based on the magnetic field distribution, results in an ill-conditioned inverse problem, and thus several solutions are suggested.

By way of example, against the ill-conditioned inverse problem, a method that uses a constrained term referred to as a regularization term is employed in many cases (Bertero M and Boccacci P, Introduction to inverse problems in imaging, IOP Publishing, 1998).

In the method employing the constrained term for regularization, an error function e(χ) as indicated in the following formula 3 is used, and a susceptibility image where the error function is minimized is obtained.

[Formula 3]

$$e(\chi) = \|W(\delta - C\chi)\|_2^2 + \lambda \|G\chi\|_2^2 \qquad (3)$$

where δ is a column vector of the magnetic field image, χ is a column vector as a candidate of the susceptibility image, C is a matrix corresponding to a convolution calculation for χ, W is a weight, λ is a constant freely selectable, and G is a differential operator. In the formula 3, the second term is a regularization term, representing a constraint for smoothing a susceptibility value, and this may reduce noise and artifacts.

There has been described so far a general method for calculating the susceptibility.

In subcutaneous fat near the prostate gland, it is conceivable that degradation in accuracy due to a loss of signals becomes more pronounced, because there are signal-undetectable regions around the subcutaneous fat, such as outside-body parts and thighbones. Since the accuracy degradation in calculating the susceptibility may propagate into an adjacent region, there is a possibility that the calculation accuracy may also be reduced in a water region around the subcutaneous fat. Such reduction of calculation accuracy may cause inhomogeneity of susceptibility values in the water region around the subcutaneous fat. When the susceptibility is calculated under the smoothing constraint as indicated by the formula 3, noise or artifacts can be reduced, but it is difficult to reduce the accuracy degradation in the fat region or inhomogeneity of the water region, due to the signal loss.

In the present embodiment, the susceptibility of the fat region and that of the water region are calculated individually, so that a reduction of the calculated fat susceptibility does not propagate into the surroundings, in order to reduce the accuracy degradation in the subcutaneous fat region and its surroundings in the prostate susceptibility map. Specifically, a fat content image is calculated according to a water-fat separation process, the region is divided into a fat region and a water region by using the fat content image, the susceptibility of the fat region and that of the water region are calculated individually, and finally they are combined. In the water region, assuming the air region and the fat region as backgrounds, background magnetic field is removed to calculate the susceptibility of the water region. In the fat region, in order to improve the calculation accuracy, the susceptibility is calculated under the constraints that no inhomogeneity of susceptibility occurs in the water region.

Figure 6:
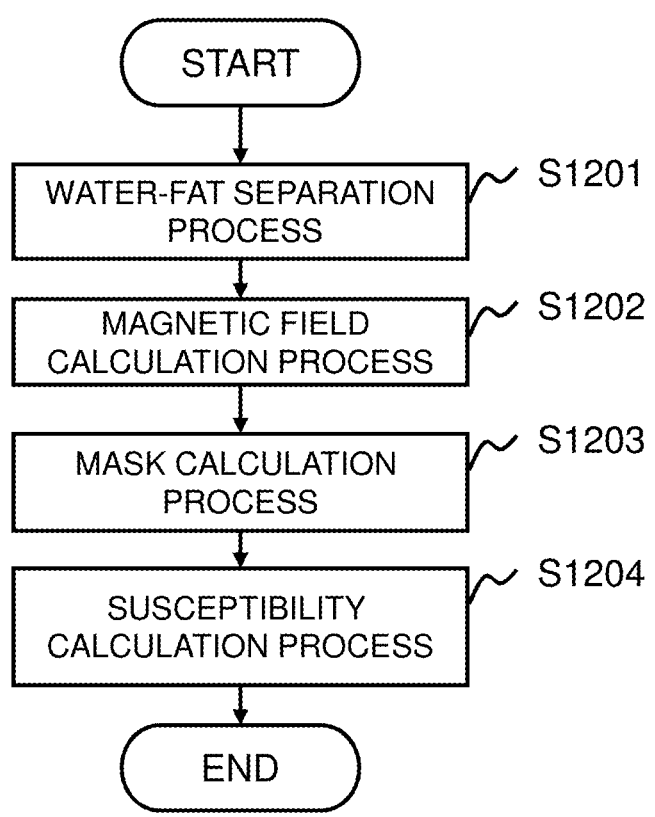
FIG. 6 is a flowchart of an image conversion process according to the first embodiment.
Figure 7:
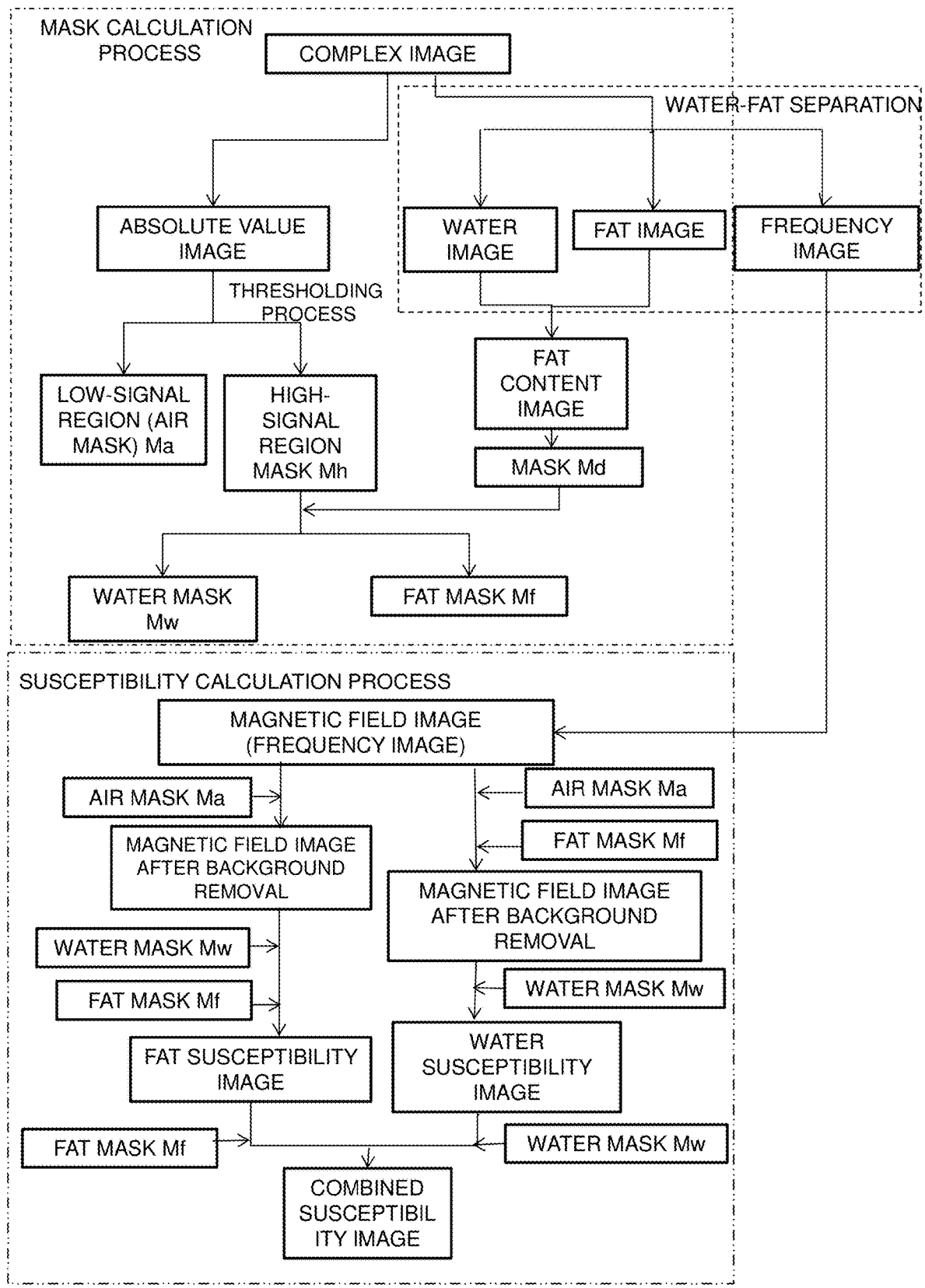
FIG. 7 illustrates a relationship between images and masks, used in calculating the masks and in calculating susceptibility according to the first embodiment.

With reference to FIGS. 6 and 7, the image conversion process S1103 of the present embodiment will be described in detail. FIG. 6 shows a processing flowchart, and FIG. 7 illustrates a relationship between generated images and masks. As shown in FIG. 6, the image conversion process in the present embodiment includes four steps; a water-fat separation process S1201, a magnetic field calculation process S1202, a mask image calculation process S1203, and a susceptibility image calculation process S1204.

[Water-Fat Separation (S1201)]

Firstly, there will be described a processing flow of the water-fat separation process S1201 in the present embodiment. The water-fat separation processor 510 of the present embodiment performs fitting, to fit signal values obtained by measurement to a signal model represented by water, fat, $R_2^*$ (apparent transverse magnetization relaxation rate commonly used for water and fat), and an offset frequency distribution, thereby calculating the water image, the fat image, and the frequency image, according to the water-fat separation process (the process within the dotted rectangle in FIG. 7). The offset frequency indicates an offset amount of resonance frequency that varies spatially due to static magnetic field inhomogeneity, or the like, and the frequency image is an image having those offset frequencies as pixel values. Here, the "water image" and the "fat image" indicate, respectively, an image where signals from water protons are dominant and an image where signals from fat protons are dominant.

Figure 8:
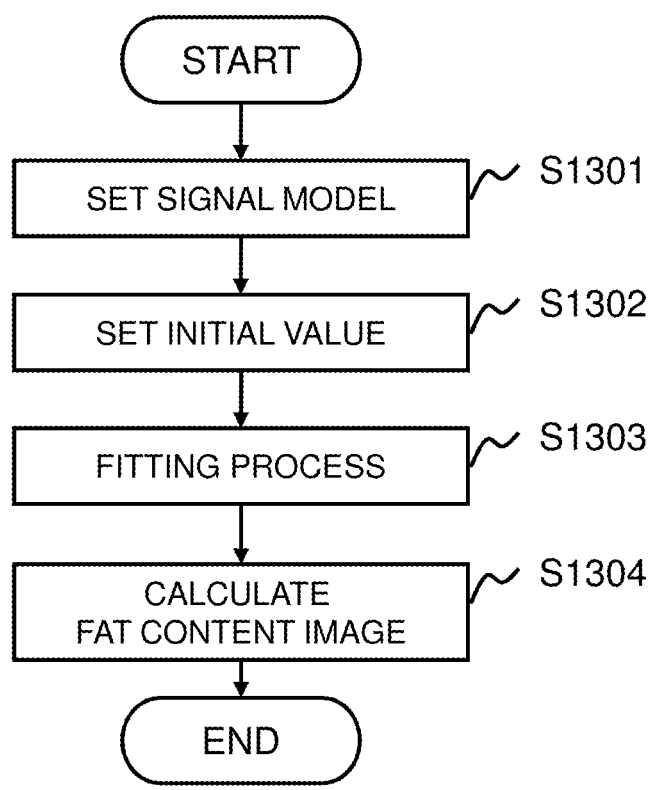
FIG. 8 is a flowchart of a water-fat separation process according to the first embodiment.

FIG. 8 is a flowchart showing the water-fat separation process of the present embodiment. Firstly, there is provided a signal model representing signal value variations according to echo times (step S1301). Next, various initial values are set for the fitting process that will be described below (step S1302). Then, by using original images $I_n$ at $N_e$ various echo times ($N_e$ is an integer at least three), the initial value, and the signal model, the fitting process is performed for fitting the measured signal to the signal model according to a non-linear least squares method (step S1303), thereby calculating the water and fat frequency images. Finally, a fat content image is calculated from thus obtained water image and the fat image (step S1304). There will now be described details of each processing.

Initially, signal model setting of step S1301 will be described. In the present embodiment, there is provided a signal model using as fitting variables, water signal intensity, fat signal intensity, offset frequency, and apparent relaxation rate $R_2^*$. Formula 4 expresses the signal model $s'_n$ representing signal intensity $s_n$ (n=1, ..., $N_e$) at any pixel, in the image $I_n$ reconstructed from the echo signals acquired at the n-th echo time $t_n$.

[Formula 4]

$$s'_n = (\rho_w + K_n \rho_f) e^{-R_2^* t_n} e^{i2\pi\psi t_n} \quad (4)$$

where $t_n$ is the n-th echo time, $\Psi$ is the offset frequency, $\rho_w$ and $\rho_f$ are complex signal intensity of water and fat, respectively, $K_n$ is the amount of phase change (complex number) of the fat signal at the time point $t_n$, $R_2^*$ is an apparent transverse magnetization relaxation rate commonly used by water and fat. It is to be noted that the signal model in step S1301 is not limited to the form as expressed by the formula 4. For example, in the case where the number of acquired echoes is small, it is possible to configure a signal model having only the water signal intensity, the fat signal intensity, and the offset frequency as the fitting variables.

The fat signal is known as having a plurality of spectrum peaks, according to its molecular structure. Therefore, when the fat signal having P peaks (P is an integer at least one) is considered, the amount of phase change $K_n$ of the fat signal is expressed by using the following formula 5:

[Formula 5]

$$K_n = \sum_{p=1}^{P} a_p e^{-i2\pi f_p t_n} \quad (5)$$

where $a_p$ and $f_p$ represent, respectively, relative signal intensity and a frequency difference from water, of the p-th fat peak (p is an integer satisfying $1 \leq p \leq P$). It should be noted that "$a_p$" satisfies the conditions as expressed by the formula 6:

[Formula 6]

$$\sum_{p=1}^{P} a_p = 1 \quad (6)$$

Hereinafter in the present embodiment, there is employed a signal model where fat has six peaks (P=6).

Next, there will be described a method for setting initial values in step S1302. The initial values to be provided are; complex signal intensity of water and complex signal intensity of fat of each pixel, the offset frequency distribution, and the apparent transverse magnetization relaxation rate $R_2^*$. For the initial values of the water complex signal intensity $\rho_w$ and of the fat complex signal intensity $\rho_f$ in each pixel, a value $|s_n|_{max}$ is used. This value is obtained by subjecting the absolute value $|s_n|$ to maximum intensity projection (MIP) in the time direction, where $|s_n|$ is the absolute value of a signal value $s_n$ in the original image obtained by actual measurement. The initial value of the offset frequency distribution is zero in all the pixels. The initial value of the apparent transverse magnetization relaxation rate $R_2^*$ is 1 in all the pixels.

The initial values of the water and fat complex signal intensity $\rho_w$ and $\rho_f$ in each pixel, the initial value of the offset frequency distribution, and the initial value of the apparent transverse magnetization relaxation rate $R_2^*$ are not necessarily those values as described above, and any values may be used as far as a result of computation according to the non-linear least squares method may neither diverge nor vibrate.

Next, there will be described the fitting process in step S1303. In the present embodiment, variables used for estimating true values by fitting are assumed as the following in each pixel; $\rho_w$ is the water signal intensity, $\rho_f$ is fat signal intensity, $R_2^*$ is the apparent transverse magnetization relaxation rate, and $\Psi$ is the offset frequency. Furthermore, the estimates of the variables are assumed as $\rho_w'$, $\rho_f'$, $R_2^{*\prime}$, and $\Psi'$, respectively, and differences between the true values and the estimates are assumed as $\Delta\rho_w$, $\Delta\rho_f$, $\Delta R_2^*$, and $\Delta\Psi$, respectively. When a signal value obtained by actual measurement is $s_n$ and an estimated signal is $s'_n$ that is obtained by substituting the estimates values $\rho_w'$, $\rho_f'$, $R_2^{*\prime}$, and $\Psi'$ into the signal model expressed by formula 4, the difference $\Delta s_n$ between the measured signal $s_n$ and the estimated signal $s'_n$ is expressed by the following formula 7:

[Formula 7]

$$\Delta s = Ax \quad (7)$$

where $$\Delta s = \begin{bmatrix} \Delta s_1 \\ \vdots \\ \Delta s_N \end{bmatrix}, x = \begin{bmatrix} \Delta \rho_w \\ \Delta \rho_f \\ \Delta \psi \\ \Delta R_2^* \end{bmatrix}, A = \begin{bmatrix} \frac{\partial s'_1}{\partial \rho_w} & \frac{\partial s'_1}{\partial \rho_f} & \frac{\partial s'_1}{\partial \psi} & \frac{\partial s'_1}{\partial R_2^*} \\ \vdots & \vdots & \vdots & \vdots \\ \frac{\partial s'_N}{\partial \rho_w} & \frac{\partial s'_N}{\partial \rho_f} & \frac{\partial s'_N}{\partial \psi} & \frac{\partial s'_N}{\partial R_2^*} \end{bmatrix}$$

Therefore, vector x can be calculated by using pseudo-inverse matrix of matrix A, according to the following formula 8:

[Formula 8]

$$x = (A^H A)^{-1} A^H \Delta s \quad (8)$$

where $A^H$ is a complex conjugate transposed matrix of the matrix A.

In the fitting process S1303 in the present embodiment, $\Delta\rho_w$, $\Delta\rho_f$, $\Delta R_2^*$, and $\Delta\Psi$ being the elements of the difference vector x obtained by the formula 8 are added to the estimates $\rho_w'$, $\rho_f'$, $R_2^{*\prime}$, $\psi'$, respectively, and the estimated signal $s'_n$ is recalculated. Then, the formula 8 is used to calculate the difference vector x again. By repeating those procedures, the difference vector x is minimized, allowing the estimates to approach the true values. In the fitting process of the present embodiment, any threshold may be set, and the procedures above are repeated until the norm of the difference vector x becomes less than or equal to the threshold. Then, the finally obtained water signal intensity $\rho_w'$, fat signal intensity $\rho_f'$, apparent transverse magnetization relaxation rate $R_2^{*\prime}$, and offset frequency $\Psi'$ of each pixel may become the water image, the fat image, the $R_2^*$ image, and the frequency image, respectively. As the nonlinear least squares method, any publicly known methods may be applicable, such as Levenberg-Marquardt method.

Next, a fat content image is calculated from the water image and the fat image obtained by the fitting process S1303 (step S1304). The fat content image is an image where a value of each pixel represents a fat content. In the present embodiment, each pixel value representing the fat content is calculated by dividing the pixel value of the fat image by the sum of the pixel value of the water image and the pixel value of the fat image. The fat content image is used as a discriminant image in calculating a fat mask, in the mask calculation process described in the following.

In the aforementioned water-fat separation process S1201, four unknown quantities; the water image, the fat image, the frequency image, and the $R_2^*$ image, are obtained by using four echoes at four different echo times. However, the $R_2^*$ image is not necessarily obtained. Therefore, the process of the present embodiment can be applied to the case where the number of echoes $N_e$ at different echo times is three or more.

Furthermore, as for the frequency image, even though the number of echoes is just one, each pixel value $\Psi'$ of the frequency image can be calculated according to the following formula 9, by using each pixel value $I_1(r)$ of the original image $I_1$ and the echo time $t_1$.

[Formula 9]

$$\psi'(\vec{r}) = -\arg(I_1(\vec{r}))/(2\pi t_1) \quad (9)$$

where arg(c) is an argument of the complex number c.

When the number of echoes is two, the frequency image can be calculated according to the following formula 10, by using the pixel values ($I_1(r)$ and $I_2(r)$) respectively of the first original image $I_1$ and of the second original image $I_2$ and the echo times $t_1$ and $t_2$:

[Formula 10]

$$\psi'(\vec{r}) = -\arg(I_2(\vec{r})/I_1(\vec{r}))/\{2\pi(t_2-t_1)\} \quad (10)$$

Therefore, it is also possible to perform the process for acquiring the frequency image, separately from the water-fat separation process according to the aforementioned fitting process.

[Magnetic Field Calculation Process (S1202)]

Next, the magnetic field calculation process as described below is applied to thus calculated frequency image $\Psi'$, thereby calculating a magnetic field image $\delta$ (step S1202). The magnetic field image is an image that depicts relative magnetic field variations normalized by a static magnetic field image. The magnetic field calculator 520 transforms the frequency image $\Psi'(r)$ according to the following formula 11, whereby the magnetic field image Y(r) is calculated.

[Formula 11]

$$\delta(\vec{r}) = 2\pi \psi'(\vec{r})/\gamma B_0 \quad (11)$$

where γ is a gyromagnetic ratio of protons, and $B_0$ is static magnetic field strength.

[Mask Calculation Process (S1203)]

Next, a mask calculation processing flow S1203 of the present embodiment will be described. The mask calculator 530 of the present embodiment calculates a low-signal region mask showing a low-signal region such as air, and a water mask representing a region where water is dominant within a voxel, and a fat mask showing a region where fat is dominant within a voxel, from the complex images calculated by the image reconstructor 400 and the water image and the fat image calculated by the water-fat separation processor 510. As shown in FIG. 3, the mask calculator 530 includes a low-signal region mask calculator 531, a fat mask calculator 532, and a water mask calculator 533.

Figure 9:
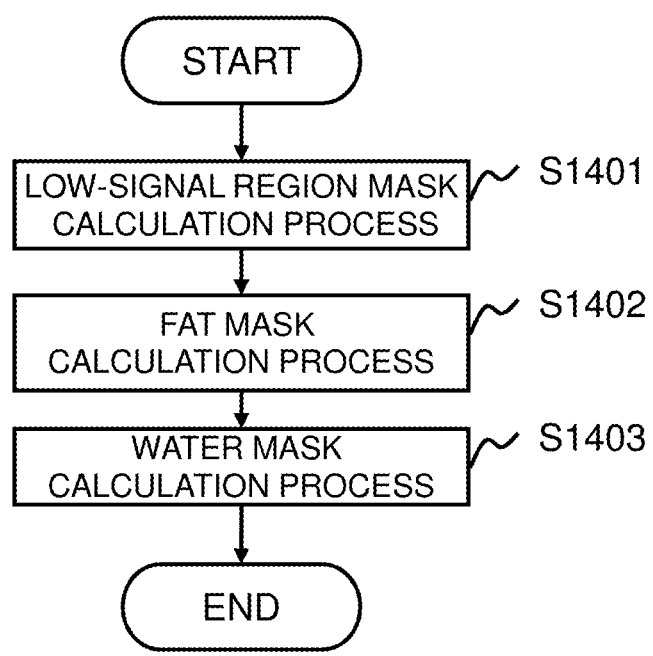
FIG. 9 is a flowchart of a mask calculation process according to the first embodiment.

FIG. 9 is a processing flowchart of the mask calculator 530 of the present embodiment. In the present embodiment, firstly, a mask-specific absolute value image is calculated from the complex image, and a low-signal region mask and a high-signal region mask are calculated from the mask-specific absolute value image (step S1401). Next, a fat mask is calculated from the high-signal region mask and the fat content image calculated in the aforementioned step S1304 (step S1402). Finally, a water mask is calculated from the high-signal region mask and the fat mask (step S1403). Details of each processing will be described below.

Firstly, the low-signal region mask calculation method of the step S1401 will be described (a process in the dash-dotted-line rectangle in FIG. 7). Firstly, the mask-specific absolute value image is calculated. The mask-specific absolute value image is an image having pixels represented by real numbers equal to or larger than zero. In the present embodiment, the mask-specific absolute value image is assumed as one absolute value image, obtained by calculating the root sum square in the time direction as to each pixel in the absolute value images of all the echoes. Any method is applicable for calculating the mask-specific absolute value image. For example, the mask-specific absolute value image may be the absolute image of the first echo.

Next, the low-signal region mask is calculated from the mask-specific absolute value image. In the present embodiment, the low-signal region mask Ma is calculated from the mask-specific absolute value image according to thresholding. A predetermined threshold is used for the low-signal region mask, and a region where the pixel value of the mask-specific absolute value image is equal to or smaller than the threshold is set to 1, and a region having that pixel value larger than the threshold is set to zero. The threshold may also be obtained by using a method such as a discriminant analysis method, from a distribution of all the pixel values in the absolute value image. It is further possible to perform an image processing such as isolated point removal, subsequent to the thresholding. There are various low-signal region mask calculation methods. By way of example, boundaries inside and outside the body are detected, and a region inside the body may be set to zero, and a region outside the body may be set to 1, according to detection results. Such alternative methods may be applicable as a noise masking process.

Then, a high-signal region mask Mh is calculated by subtracting the pixel value of the low-signal region mask from 1, with respect to each pixel.

Next, the fat mask calculation method in step S1402 will be described. In the present embodiment, the high-signal region mask Mh should be divided into a fat mask Mf and a water mask Mw, and an image (a discriminant image) for discriminating between them is prepared to create a discriminant mask. Here, the fat content image calculated in the water-fat separation process S1201 (S1304) is used as the discriminant image, and thresholding is performed using a certain threshold value, thereby calculating the discriminant mask Md. By way of example, a region where the fat content is higher than the threshold is set to 1, and a region where the fat content is equal to or lower than the threshold is set to zero. In the present embodiment, the threshold is set to 0.8. The high-signal region mask Mh is multiplied by thus calculated discriminant mask Md, and thus the fat mask Mf is calculated.

Any method may be used for calculating the fat mask, and the fat image can be calculated by a method such as subjecting the fat image to thresholding, for instance. In this case, the fat content image calculation process (FIG. 8, S1304) in the water-fat separation process (FIG. 6, S1201) can be omitted. Additional processing may be performed to obtain the fat mask after the thresholding; the isolated point removal process and/or a process of setting a fat region having a value equal to or less than a certain threshold to zero. By adding such processes, it is possible to remove the region that is determined as the fat region due to noise.

Finally, the water mask Mw is calculated (step S1403). In the present embodiment, the water mask Mw is calculated by subtracting the fat mask Mf from the high-signal region mask Mh. Any method for calculating the water mask may be used, and the water image can be calculated by a method such as thresholding the water image, for instance.

In the present embodiment, the pixel values of the low-signal region mask Ma, the fat mask Mf, and the water mask Mw are set to 0 or 1, but any other numbers may be used. For example, the fat mask may be calculated through multiplication of the fat content image by the high-signal region mask, and the water mask may be calculated through multiplication of an image obtained by subtracting the fat content from 1, as to each pixel, by the high-signal region mask.

[Susceptibility Calculation Process S1204]

Next, there will be described the susceptibility calculation process (the process in the chain double-dashed rectangle in FIG. 7) in the present embodiment. As shown in FIG. 3, the susceptibility calculator 540 of the present embodiment calculates a susceptibility image, from the low-signal region mask, the water mask, and the fat mask calculated in the mask calculator 530, and the magnetic field image calculated in the magnetic field calculator 520. For this purpose, as show in FIG. 3, the susceptibility calculator 540 includes a background magnetic field remover 541, a fat susceptibility calculator 542, a background magnetic field remover 543, a water susceptibility calculator 544, and a combined susceptibility calculator 545.

Figure 10:
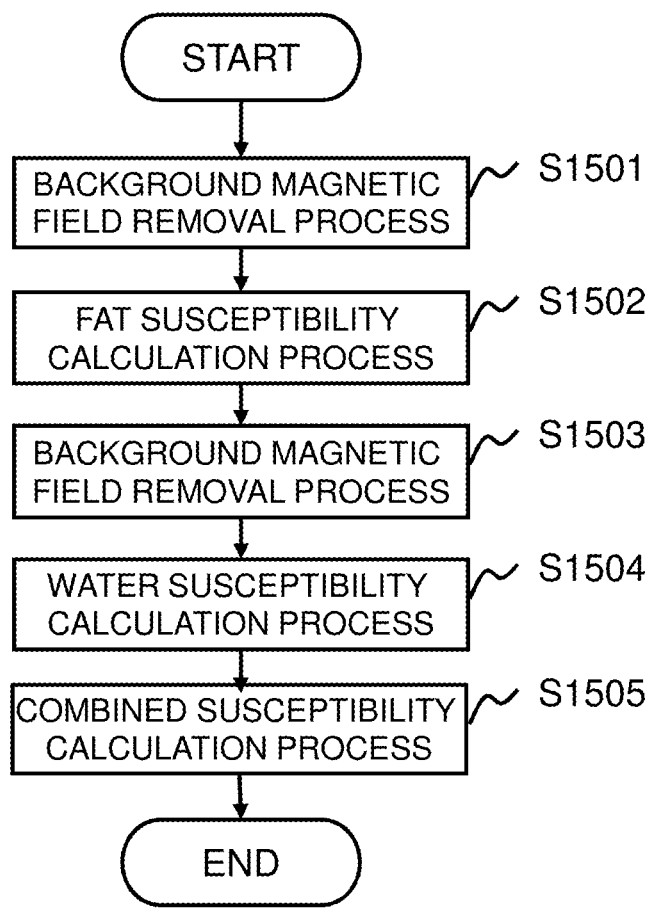
FIG. 10 is a flowchart of a susceptibility calculation process according to the first embodiment.

With reference to the flowchart as shown in FIG. 10, the processing S1204 of the susceptibility calculator 540 of the present embodiment will be described in detail. The steps S1501 to S1505 in FIG. 10 correspond respectively to the processes of the components 541 and 545 in the susceptibility calculator 540. In the present embodiment, firstly the background removal process is performed on the magnetic field image, assuming the region defined by the low-signal region mask as a background region (step S1501). Next, the susceptibility calculation process is performed from the image where the background has been removed in S1501, and calculates the fat susceptibility image under the constraints that values in the water region become zero (step S1502). Next, the background removal process is performed on the magnetic field image, assuming the region defined by the low-signal region mask and the fat mask as the background region (step S1503). Then, the susceptibility calculation process is performed from the image where the background has been removed in S1503, and calculates the water susceptibility image (step S1504). Finally, the fat susceptibility image and the water susceptibility image are combined, thereby calculating a combined susceptibility image (step S1505). Each of the processes above will now be described in detail.

Firstly, in step S1501, background magnetic field removal is performed on the magnetic field image δ calculated in the magnetic field calculation process S1202, assuming the region defined by the low-signal region mask as the background region. Any method may be employed for the background magnetic field removal, and in the present embodiment, the SHARP method is employed.

Specifically, the magnetic field generated from the background region satisfies a characteristic of harmonic function within the region of interest (the region defined by the high-signal region mask calculated by the mask calculation process S1203), and this is utilized to solve the following equation in the region of interest, according to the methods such as TSVD (Truncated Singular Value Decomposition) and the least squares method, thereby calculating a local magnetic field:

[Formula 12]
$$MH\delta_{local} = MH\delta_{total} \quad (12)$$

where M is an orthogonal matrix having a binary mask (high-signal mask) as diagonal components where the region of interest is set to 1, H is a matrix representing a convolution calculation, $\delta_{local}$ is a column vector of the local magnetic field image (the magnetic field δ' after the background removal), $\delta_{total}$ is a column vector of the magnetic field image before the background removal (the magnetic field image δ calculated in the magnetic field calculation process S1202). Here, the region of interest represents a region defined by the diagonal components of M, and the background region represents a region that is defined by the diagonal components of I−M, assuming I as a unit matrix.

Next, in step S1502, the fat susceptibility image χf is calculated from the magnetic field image obtained after the background magnetic field removal in S1501, under following constraints; a smoothing constraint for smoothing the susceptibility and a specific-value constraint for setting susceptibility of a specific region to a specific value. The specific region here indicates the region defined by the water mask, and the specific value is assumed as zero.

There will now be described a specific example of the method for calculating the susceptibility image χf, including the smoothing constraint and the specific-value constraint.

In one of the specific examples, as expressed by the formula 13, an object function is minimized, having a smoothing constraint term with the constraint for smoothing the susceptibility and a specific-value constraint term with the constraint for setting the susceptibility of the specific-value region to a specific value, whereby the fat susceptibility image χf is calculated.

[Formula 13]
$$\chi_f = \mathrm{argmin}_{\chi_f} \|M(C\chi_f - \delta')\|_2^2 + \lambda_w \|M_w \chi_f\|_2^2 + \lambda_f \|M_f G \chi_f\|_2^2 \quad (13)$$

where $\|a\|_2^2$ represents the square of L2 norm of a certain vector a

In addition, C is an operator representing a convolution calculation and G is a differential operator. M is the high-signal region mask, δ' is the magnetic field where background is removed in S1501, Mw is the water mask, and Mf is the fat mask. The first term in the formula 13 is a term for minimizing an error in the relational expression between the susceptibility and the frequency, assuming the inside of the mask M as the region of interest, the second term placing the constraint that the water region is set to zero, and the third term is a term for smoothing inside of the fat. Magnitude of the constraints is defined by λw and λf, respectively, and they may be any constants. Hereinafter, λw will be referred to as a specific-value parameter, and λf will be referred to as a smoothing parameter.

Preferably, the specific-value parameter λw defining the magnitude of the specific-value constraint, and the smoothing parameter λf defining the magnitude of the smoothing constraint may be set to values that maximize the ratio between their average value and standard deviation within the fat mask of the fat susceptibility image, from the viewpoint that an effect of accuracy improvement in the second term and an effect of noise reduction in the third term are maximized. Those parameters may be determined according to any method. By way of example, those parameters may be set to any predetermined values.

It is to be noted that in the present embodiment, λw is set to equal to or less than a predetermined value ($\lambda_{wth}$). In the Non Patent Document 3, there is disclosed a method of calculating the susceptibility inside the brain, under the constraints that after the background magnetic field removal assuming the region outside the brain as the background region, the susceptibility outside the brain being the background region is set to zero. In this method, there is added a constraint to set zero to the background region where contribution of the susceptibility has been removed according to the background magnetic field removal process, and therefore, a regularization parameter of the regularization term used for the constraint is large, that is, $10^{20}$. On the other hand, in the formula 13, the water region on which the constraint should be placed, is not the background region. Therefore, such too large specific-value parameter may cause accuracy degradation of the calculated susceptibility in the water region, resulting in accuracy degradation of the susceptibility in the surrounding fat region. Setting the value of λw to be equal to or less than the predetermined value ($\lambda_{wth}$) may prevent the accuracy degradation, allowing reduction of calculation time required for the parameter search. It is to be noted that $\lambda_{wth}$ may vary in response to the values of M and W used in the first term, but in the present embodiment, $\lambda_{wth}$ may be set to 10, for instance.

The equation of formula 13 can be minimized through the iterative operation using the method such as the conjugate gradient method. In this situation, the initial vector may be any value, and for example, zero vector may be used. Any conditions are conceivable for terminating the iterative operation, and for example, there may be a method that terminates the iterative operation when the iteration count exceeds a predetermined threshold. According to the calculation method using the formula 13, the susceptibility is calculated under the constraint that no inhomogeneity occurs in the water region by using the second term, whereby accuracy in calculating the fat susceptibility can be improved.

In the first term in the formula 13, weight W may be employed instead of the mask M. Usually, the weight W is defined within the region of interest where the background region has been removed, and it is calculated on the basis of a phase image, for instance (the method described in the Japanese Unexamined Patent Application Publication No. 2015-62637 according to the inventors of the present invention). Specifically, phase fluctuation of each pixel is calculated from a phase image P, and the weight W is calculated based on the magnitude of thus calculated phase fluctuation. By way of example, the weight W is calculated in a manner that the larger is the phase fluctuation, the smaller is the weight W. For the phase fluctuation, a statistical index such as standard deviation is used, which is calculated using pixel values (phase values) of a plurality of pixels in the surrounding region of a target pixel as to which the phase fluctuation is calculated.

The next formula 14 may also be used, instead of the formula 13, for calculating the fat susceptibility, for example:

[Formula 14]

$$\chi_f = \mathrm{argmin}_{\chi_f} \|M(CM_f\chi_f - \delta')\|_2^2 + \lambda_f \|M_f G\chi_f\|_2^2 \quad (14)$$

In the formula 14, Mf is used in the first term, whereby the specific-value constraint can be placed for setting zero to the susceptibility of the water region. The second term is a smoothing constraint similar to the third term of the formula 13. Instead of Mf in the first term, weight function Mf' may be used so that the water region has any constant $c_w$ (e.g., 0.2), and the fat region has any constant $c_f$ (e.g., 0.8) ($c_w < c_f$).

There is still another susceptibility calculation method for calculating the susceptibility image. In this method, an updating process and a smoothing process are performed alternately, where the updating process updates a solution based on the error function defined by a predetermined initial susceptibility distribution $\chi_{f0}$ and the magnetic field distribution δ (the method described in the Japanese Patent Application No. 2014-228843, WO 2016/076076 according to the inventors of the present invention; hereinafter referred to as "new susceptibility calculation method").

Specifically, the following process is performed repeatedly; an updated susceptibility distribution $\chi_{UPD}$ is calculated from the magnetic field distribution δ and the initial susceptibility distribution $\chi_{f0}$, the updated susceptibility distribution $\chi_{UPD}$ is smoothed to calculate a susceptibility distribution after filtering process (a processed susceptibility distribution) $\chi_{SMT}$, the updated susceptibility distribution $\chi_{UPD}$ and the processed susceptibility distribution $\chi_{SMT}$ are combined to calculate a combined susceptibility distribution $\chi_{ADD}$, and when it is determined to terminate the iterative operation, the initial susceptibility distribution $\chi_{f0}$ is updated to the combined susceptibility distribution $\chi_{ADD}$.

The updated susceptibility distribution $\chi_{UPD}$ is calculated from the initial susceptibility distribution $\chi_{f0}$, by using the error function $e(\chi_{f0})$ as expressed by the following formula:

[Formula 15]

$$e(\chi_{f0}) = \|M(CM_f\chi_{f0} - \delta')\|_2^2 \quad (15)$$

A gradient $\Lambda e(\chi_{f0})$ of the error function $e(\chi_{f0})$ is calculated according to the formula 15, and by using thus calculated gradient $\Lambda e(\chi_{f0})$, the updated susceptibility distribution $\chi_{UPD}$ is calculated according to formula 16:

[Formula 16]

$$\chi_{UPD} = \chi_{f0} + \Lambda e(\chi_{f0}) \quad (16)$$

Any susceptibility distribution may be set as the initial susceptibility distribution $\chi_{f0}$ that is provided initially. By way of example, the susceptibility distribution where all the values are set to zero may be used as the initial susceptibility distribution $\chi_{f0}$. In the processing above, Mf is used in the formula 15, placing the constraint that sets the susceptibility of the water region to zero. Instead of Mf in the formula 15, weight function Mf' may be used so that the water region has any constant $c_w$ (e.g., 0.2), and the fat region has any constant $c_f$ (e.g., 0.8) ($c_w < c_f$).

The processed susceptibility distribution $\chi_{SMT}$ is calculated by applying an edge preserving smoothing filter (the filter as described in the publication of WO 2016/076076) to the updated susceptibility distribution $\chi_{UPD}$ to perform smoothing (a process corresponding to the smoothing constraint). This edge preserving smoothing filter serves as a filter featured in that smoothing is applied intensively in a region where a local dispersion is small, whereas smoothing is applied not intensively in a region where the local dispersion is large, and therefore, this allows maintaining of a quantitative value of the susceptibility and preserving an edge part including a microscopic section image. The smoothing may be applied only to the fat region.

The combined susceptibility distribution $\chi_{ADD}$ is calculated by combining the updated susceptibility distribution $\chi_{UPD}$ with the processed susceptibility distribution $\chi_{SMT}$. Specifically, Fourier transform is applied to the updated susceptibility distribution $\chi_{UPD}$ and the processed susceptibility distribution $\chi_{SMT}$, respectively, so as to obtain k-space data. Each of the thus transformed k-space data items (Fourier components) is weighted, and thus weighted k-space data items are added. Then, after the addition, a combined susceptibility distribution $\chi_{ADD}$ is obtained by the inverse Fourier transform.

Weighting the k-space is performed by creating a weighting image G(k) (k indicates a data position in the k-space, the same shall apply hereafter), and multiplying the k-space data by the weighting image G. In this situation, the weighting image $G_{UPD}$ by which the k-space data obtained from the updated susceptibility distribution $X_{UPD}$ is multiplied, is configured in a manner that the weight given to the data in proximity to a magic angle region is set to be smaller than the weight given to the other region, for instance. On the other hand, the weighting image $G_{SMT}$ by which the k-Space Data Obtained from the processed susceptibility distribution $X_{SMT}$ is multiplied, is configured in a manner that the weight given to the data in proximity to the magic angle region is set to be larger than the weight given to the other region. As the weighting images $G_{UPD}(k)$ and $G_{SMT}(k)$ satisfying the conditions above, the weighting image defined by the following formula 17 may be employed, for example, using the Fourier component D(k) in the point-dipole magnetic field and an adjusting parameter b for adjusting the magnitude of the magic angle region:

[Formula 17]

$$G_{UPD}(k) = \begin{cases} 1 & \text{if } |D(k)| \geq b \\ |D(k)|/b & \text{if } |D(k)| < b \end{cases} \quad (17)$$

$$G_{SMT}(k) = 1 - G_{UPD}(k)$$

In the formula 17 above, a region where a value of the Fourier component is smaller than a predetermined value (b) in the updated susceptibility distribution $\chi_{UPD}$ is assumed as the magic angle region.

In a minimizing process for minimizing the error function $e(\chi_{f0})$ according to the iterative operation, it is determined whether or not the iterative operation is terminated. When it is determined that the process continues, i.e., the process is repeated, the latest combined susceptibility distribution $\chi_{ADD}$ obtained at the point of time is set as the initial susceptibility distribution $\chi_{f0}$, thereby updating the initial susceptibility distribution $\chi_{f0}$. On the other hand, when it is determined as the end of the process, the latest combined susceptibility distribution $\chi_{ADD}$ at the point of time is outputted as the susceptibility distribution (in here, the fat susceptibility distribution). For example, the evaluation function $f(\chi_{UPD})$ as indicated by the following formula 18 is used, to determine the end of the process when the value of the evaluation function is smaller than a predetermined threshold $\varepsilon$.

[Formula 18]

$$f(\chi_{UPD}) = \frac{\|\chi_{UPD} - \chi_{f0}\|_2}{\|\chi_{f0}\|_2} < \varepsilon \quad (18)$$

There has been described so far a specific example of inside-the-fat susceptibility calculation process in step S1502. However, in step S1502, without limited to this specific example, any method may be employed, as far as the fat susceptibility image $\chi f$ can be calculated under the smoothing constraint that places a constraint to smooth the susceptibility and the specific-value constraint that places a constraint to assume the susceptibility in a specific region as a specific value.

In the fat susceptibility calculation S1502, according to a method such as interpolation, resolution of the input images such as $\delta'$, M, Mf, Mw (the magnetic field image after the background is removed, the high-signal mask image, the fat mask image, and the water mask image) is reduced, followed by calculating the susceptibility image $\chi f$. Then, after the calculation, the resolution of the susceptibility image $\chi f$ may be restored to the original level according to a method such as interpolation. By way of example, firstly the image size of each input image in each direction may be made half, followed by calculating $\chi f$, and after the calculation, the image size in each direction may be resumed to the original size. In the case where the fat region does is not included in a diagnostic area and high resolution is not necessary, this process allows reduction of the calculation time required for calculating $\chi f$.

Next, in step S1503, the magnetic field image $\delta$ calculated by the magnetic field calculation process S1202 is subjected to the background magnetic field removal, where a region defined by the sum of the low-signal region mask and the fat mask is assumed as the background region (step S1503). With this process, frequency change (magnetic field variations) due to a susceptibility difference between water and fat can be removed. The background magnetic field removal in step S1503 may also be performed according to any method such as the SHARP method and PDF method. For example, when the SHARP method is employed, the background magnetic field removal of the step S1503 is the same as the background magnetic field removal as described in step S1501, except that the region defined by the sum of the low-signal region mask and the fat mask is used as the background region.

Next, in step S1504, the susceptibility calculation process is performed to calculate a water susceptibility image $\chi w$, from the magnetic field image which has been subjected to the background magnetic field removal in S1503, where the region defined by the water mask is set as the region of interest. Also in step S1504, similar to the step S1502 being the fat susceptibility calculation process, any method is applicable to the susceptibility calculation, but in the present embodiment, the new susceptibility calculation method (the method described in WO 2016/076076) is employed to calculate the susceptibility. The constraint condition based on the relational expression between the magnetic field and the susceptibility is defined by the region where the water mask becomes 1. That is, instead of the aforementioned formula 15 used for the fat susceptibility calculation, the following formula 19 is employed:

[Formula 19]

$$e(\chi_{w0}) = {}_0 \|M_w(C\chi_{w0} - \delta')\|_2^2 \quad (19)$$

Other calculation methods are the same as those described by the fat susceptibility calculation method, and a process for updating a predetermined initial susceptibility distribution $\chi_{w0}$ and the smoothing process are repeated alternately. Then, the combined susceptibility distribution $\chi_{ADD}$ obtained after a predetermined number of iterative operation counts, is set as water susceptibility.

Finally, in step S1505, the fat susceptibility (inside-the-fat susceptibility image) obtained in S1502 and the water susceptibility (outside-the-fat susceptibility image) obtained in step S1504 are combined through the formula 20, and the combined susceptibility image $\chi$ is calculated (step S1505).

[Formula 20]

$$\chi = M_w \chi_w + M_f \chi_f \quad (20)$$

According to the foregoing processes (S1501 to S1505), the susceptibility calculation process (FIG. 6: S1204) is completed, and the image conversion process in step S1103 of FIG. 4 is also completed. As described above, any predetermined image processing is performed on the combined susceptibility image, and the susceptibility image (absolute value image) or the susceptibility-weighted image is created, and then it is displayed on the display part 600 (step S1104).

As described so far, the MRI apparatus of the present embodiment includes the static magnetic field magnet, the magnetic field generator that applies a gradient magnetic field and an RF magnetic field to the space formed by the static magnetic field magnet, the receiver that receives a nuclear magnetic resonance signal from a subject placed in the space, and the computer that performs computations on the nuclear magnetic resonance signal. The computer includes the measurement unit that controls operations of the magnetic field generator and the receiver and measures the nuclear magnetic resonance signal including an effect of magnetic field inhomogeneity, the image reconstructor that performs image reconstruction using the nuclear magnetic resonance signal to create a complex image, and the image converter that calculates a susceptibility image of the subject by using the complex image. The image converter includes the magnetic field calculator that calculates a magnetic field reflected image from the complex image, the mask calculator that uses the image created by the image reconstructor to calculate the low-signal region mask associated with (corresponding to) the low-signal region and a plurality of region masks associated with (corresponding to) a plurality of regions within the high-signal region, and the susceptibility calculator that uses the magnetic field reflected image calculated by the magnetic field calculator, and the low-signal region mask and the plurality of region masks calculated by the mask calculator to calculate susceptibility as to each of the plurality of regions. Under the constraint setting the low-signal region as the background, and the constraint that the susceptibility of a specific region among the plurality of regions is set to a specific value, the susceptibility calculator calculates the susceptibility of a region different from the specific region.

Furthermore, the susceptibility calculator calculates the susceptibility of the specific region, under the constraint that the low-signal region and the region different from the specific region are set as the background, and thus obtained susceptibility is combined with the susceptibility of the region different from the specific region.

The image converter of the present embodiment is further provided with the water-fat separator that uses the image generated by the image reconstructor to separate a water image where signals from water protons are dominant, and a fat image where signals from fat photons are dominant, and the mask calculator uses as a threshold, a predetermined value of fat content as to each pixel, calculated by using the water image and the fat image, to create a plurality of region masks, including the water mask that is associated with the region where the water is dominant, and the fat mask that is associated with the region where fat is dominant.

As discussed above, when the susceptibility is calculated as to each of the fat image and the water image in the MRI apparatus of the present embodiment, in the fat region, the susceptibility is calculated under the constraint that prevents inhomogeneity of the susceptibility in the water region, that is, the susceptibility is zero, thereby reducing the accuracy degradation due to a loss of signals. In the water region, after the background magnetic field removal is performed assuming the air region and the fat region as the background, the susceptibility is calculated, and thus it is possible to remove the magnetic field variations caused by the susceptibility difference between water and fat, thereby preventing inhomogeneity. In other words, the susceptibility images can be calculated both in the fat region and in the water region with a high degree of accuracy.

In the present embodiment, there has been described the MRI apparatus of horizontal magnetic field type. However, similar processes may be applicable to any types of MRI apparatus, such as an MRI apparatus of vertical magnetic field type, or other type, and similar effects may be produced. In addition, similar processes may be applied to any imaged cross section, such as a transverse section, a coronal section, a sagittal section, and an oblique section, and similar effects may be produced.

Further in the present embodiment, each of the functions of the image reconstructor, the image converter, and the display processor has been described, taking an example that those are implemented in the computer provided in the MRI apparatus, but this is not the only example. At least one of those functions may be structured on an information processor, which is independent of the MRI apparatus, and data transmittable to and receivable from the computer 209 in the MRI apparatus.

Modification Example

In the aforementioned first embodiment, there has been described that the susceptibility calculator 540 calculates the susceptibility as to each of the fat region and the water region. If the fat susceptibility is already known, the calculation may be performed, assuming the susceptibility of the fat region as a predetermined specific value. In this case, the fat susceptibility calculator 542 is not provided in the susceptibility calculator 540 in FIG. 3, and in the flowchart as shown in FIG. 10, neither the background magnetic field removal process S1501 nor the fat susceptibility calculation process S1502 are performed, and the processing details are changed as the following.

The susceptibility calculator 540 firstly performs the background removal, assuming the region defined by the low-signal region mask as the background region (S1503), and then, using the following formula, a susceptibility image $\chi$ is calculated (S1504).

[Formula 21]

$$\chi = \arg\min_{\chi} \|M(C\chi - \delta')\|_2^2 + \lambda \|G\chi\|_2^2 + \lambda_{fat} \|M_f(\chi - \Delta\chi_f e)\|_2^2 \quad (21)$$

where M is the high-signal region mask, Mf is the fat mask, $\Delta\chi f$ is a certain constant, and e is a unit vector. A predetermined susceptibility difference between water and fat, or the like, may be represented as $\Delta\chi f$. For example, it is 0.61 ppm. The second term represents a constraint for smoothing the susceptibility. The third term represents a constraint where the susceptibility in the fat region is assumed as the specific value $\Delta\chi f$. Strength of the second-term constraint and the third-term constraint are represented by $\lambda$ and $\lambda$fat, respectively.

The equation of the formula 21 can be minimized according to the iterative operation using a conjugate gradient method, or other similar methods. In this situation, the initial vector may be any value, and for example, zero vector may be used. Any conditions are conceivable for terminating the iterative operation, and for example, there may be a method that terminates the iterative operation when the iteration count exceeds a predetermined threshold.

The formula for the calculation assuming the fat susceptibility as the predetermined specific value is not limited to the formula 21. A constraint according to L1 norm may be placed in the second term.

According to this modification example, if the fat susceptibility is already known, the susceptibility in the water region may be calculated with a high degree of accuracy, by adding the third-term constraint. Thus calculated susceptibility of the water region and the fat susceptibility (specific value) are used in the formula 20 to calculate the combined susceptibility image $\chi$, similar to the first embodiment.

Second Embodiment

In the first embodiment, two high-signal region masks; fat mask and water mask, are calculated by thresholding the fat content image. Then, the susceptibility is calculated in each region, according to the different methods, and finally combined, so as to obtain the susceptibility image. In the second embodiment, the two high-signal region masks are calculated by thresholding the susceptibility image calculated in advance, instead of the fat content image. Then, followed by the processes similar to the first embodiment, the susceptibility image is obtained. There will now be described the present embodiment, focusing on the point different from the first embodiment.

The MRI apparatus of the present embodiment has basically the same configuration as the first embodiment (FIG. 2). The computer 209 of the present embodiment, similar to the first embodiment, instructs the sequencer 204 to measure echoes according to the measurement parameters and the pulse sequence set via the input device 212 (or set in advance) to measure echoes, places thus obtained echoes in k-space, performs computations on the echoes placed in the k-space to calculate a susceptibility image, and displays thus obtained image on the monitor 210. In the first embodiment, water and fat are separated as a precondition, and two or more echoes at different echo times are measured. However, in the present embodiment, the measurement may be performed at only one echo time.

Figure 11:
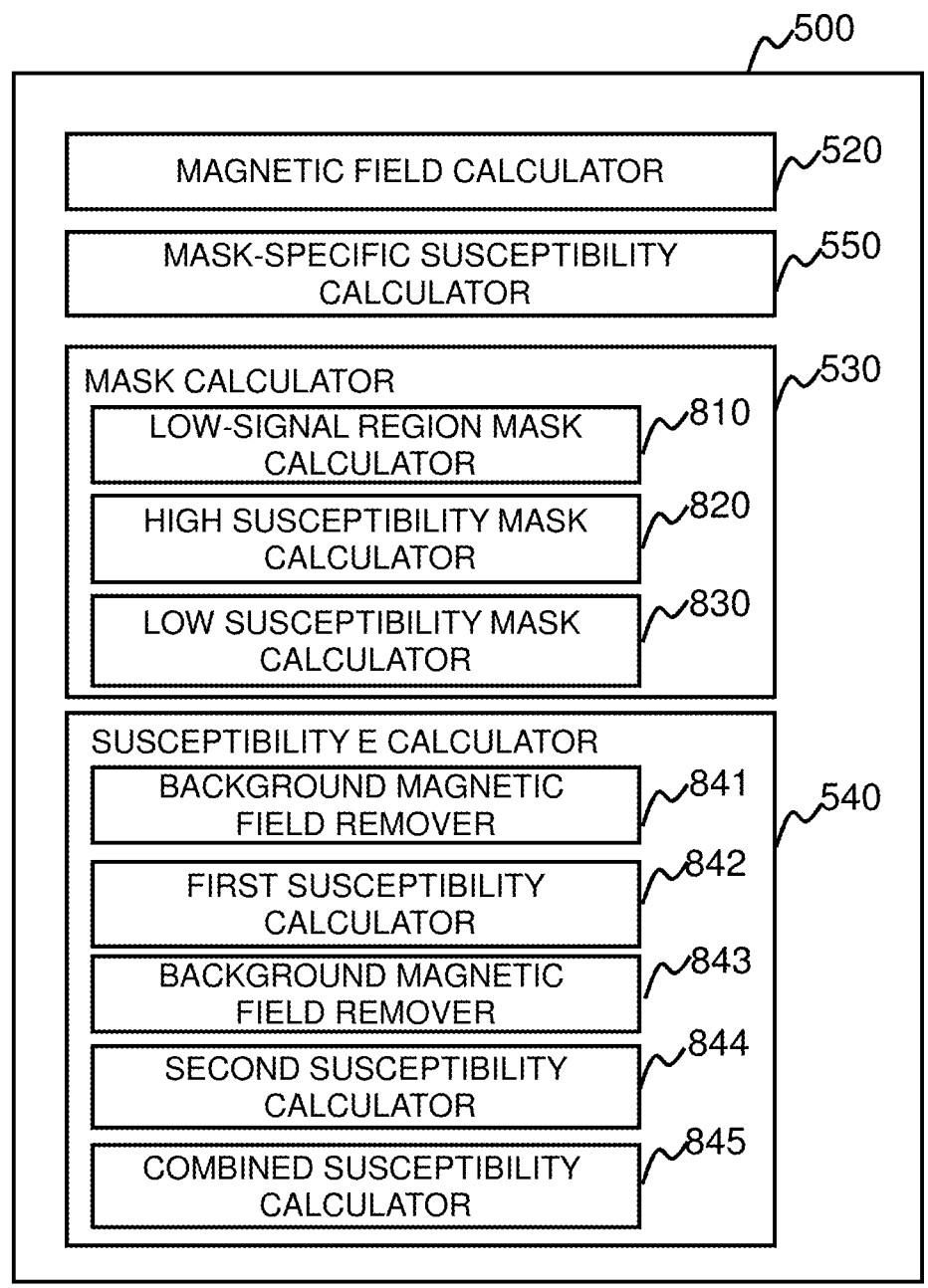
FIG. 11 is a functional block diagram of an image converter in the computer according to a second embodiment.

The computer 209 of the present embodiment also includes the measurement unit 300, the image reconstructor 400, the image converter 500, and the display processor 600, similar to the first embodiment, but the image converter 500 is configured differently. FIG. 11 is a functional block diagram showing the image converter 500 of the present embodiment. In FIG. 11, elements with the same functions as the first embodiment are labeled with the same reference numeral as FIG. 3, and they will not be redundantly explained.

As shown in FIG. 11, the image converter 500 of the present embodiment includes the magnetic field calculator 520, a mask-specific susceptibility calculator 550, the mask calculator 530, and the susceptibility calculator 540. Though not illustrated in FIG. 11, the image converter 500 of the present embodiment may also be provided with the water-fat separation processor 510, similar to the first embodiment. The mask-specific susceptibility calculator 550 may calculate a susceptibility image necessary for the processing in the mask calculator 530. This mask-specific susceptibility image is a provisional susceptibility image for creating masks, unlike the final susceptibility calculated by the susceptibility calculator 540. The mask calculator 530 includes a low-signal region mask calculator 810, a high susceptibility mask calculator 820, and a low susceptibility mask calculator 830. The susceptibility calculator 540 includes background magnetic field removers 841 and 843, a high susceptibility (first susceptibility image) calculator 842, a low susceptibility (second susceptibility image) calculator 844, and a combined susceptibility calculator 845.

Figure 12:
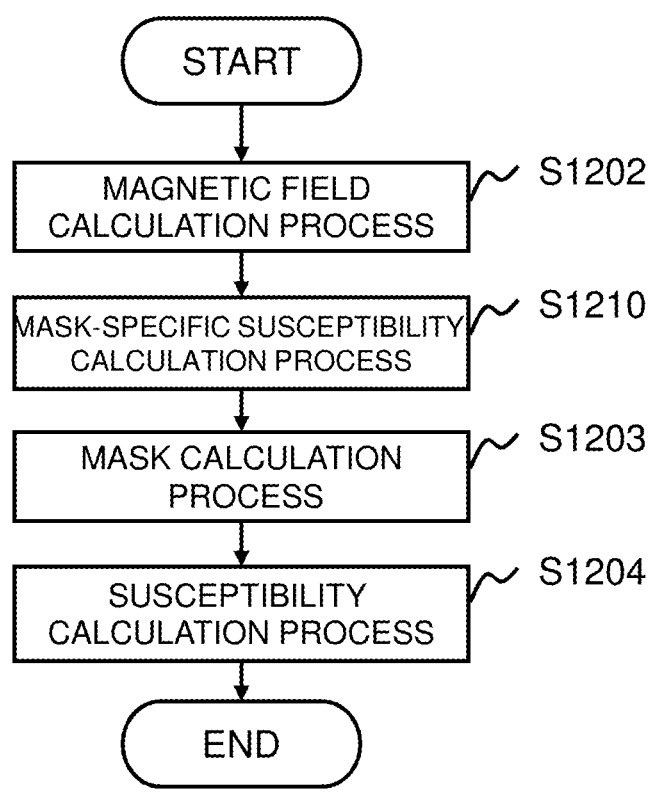
FIG. 12 is a flowchart of the image conversion process according to the second embodiment.

In light of the configurations as described above, a processing flow of the image converter 500 in the present embodiment will be described with reference to FIGS. 12 and 13. In FIG. 12, the same processes as those shown in FIG. 6 are labeled with the same reference numeral, and details will not be described redundantly.

As shown in FIG. 12, the image converter 500 of the present embodiment performs the magnetic field calculation process S1202, the mask-specific susceptibility image calculation process S1210, the mask calculation process S1203, and the susceptibility calculation process S1204.

[Magnetic Field Calculation Process (S1202)]

In the magnetic field calculation process S1202, similar to the first embodiment, a frequency image is calculated according to fitting, or by using the foregoing formulas 9 and 10, and a magnetic field image is calculated from the frequency image, according to the relational expression between a frequency and a magnetic field (Formula 11). When the frequency image is calculated according to the fitting, the number of echoes at different echo times is two or more, and water-fat separation may be performed together with calculating the frequency image.

[Provisional Susceptibility Calculation Process (S1210)]

Next in step S1210, by using the complex image calculated in the image reconstructor 400, a provisional susceptibility image is calculated (a process of the mask-specific susceptibility calculator 550). As for the mask-specific susceptibility image, the susceptibility thereof may be calculated, for example, according to the "new susceptibility calculation method" (the method described in WO 2016/076076). In this situation, a constraint condition based on the relational expression between the magnetic field and the susceptibility is defined within the region where the high-signal region mask becomes 1.

[Mask Calculation Process (S1203)]

In step S1203, three masks are calculated; i.e., a low-signal region mask representing a low-signal region such as a region of air, a high susceptibility mask representing a relatively high susceptibility region, and a low susceptibility mask representing relatively low susceptibility region, by using the complex image calculated in the image reconstructor 400, the magnetic field image calculated by the magnetic field calculator 520, and the mask-specific susceptibility image calculated by the mask-specific susceptibility calculator 550.

Figure 13:
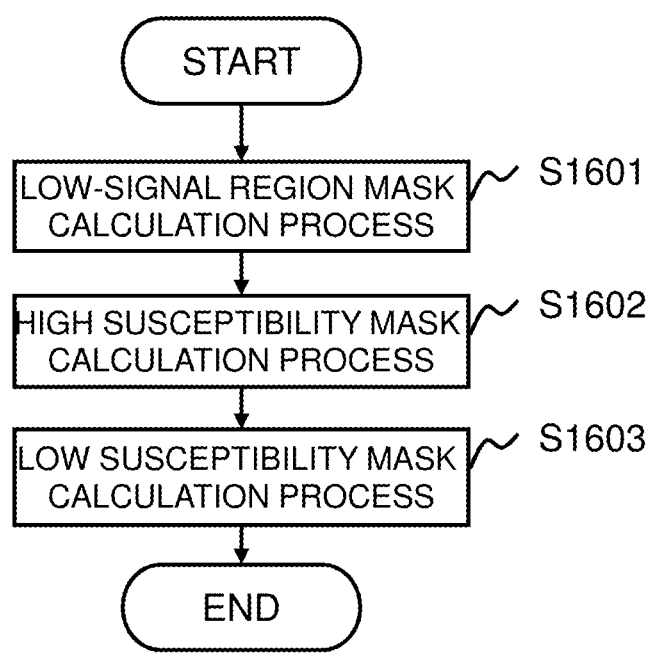
FIG. 13 is a flowchart of the mask calculation process according to the second embodiment.

FIG. 13 shows an example of flowchart of the mask calculation process. In this example, firstly, the low-signal region mask and the high-signal region mask are calculated according to a method similar to the method of the first embodiment (step S1601). Next, the high susceptibility mask is calculated from the high-signal region mask and the mask-specific susceptibility image (step S1602). Finally, the low susceptibility mask is calculated from the high-signal region mask and the high susceptibility mask (step S1603). There will now be described details of each of the processes.

The low-signal region mask calculation method of the step S1601 is basically the same as the first embodiment. Namely, a mask-specific absolute value image is calculated from the complex image, and the low-signal region mask and the high-signal region mask are calculated from the mask-specific absolute value image.

Next, in step S1602, the mask-specific susceptibility image calculated in step S1210 is assumed as a discriminant image for dividing the high-signal region, and a mask is calculated by thresholding using any threshold. That is, in the mask-specific susceptibility image, a region where the calculated susceptibility is higher than the threshold is set to 1, and a region where the calculated susceptibility is equal to or lower than the threshold is set to zero. Any value may be used as the threshold, but in the present embodiment, it is set to 0.5 ppm, for instance. Then, thus calculated mask is multiplied by the high-signal region mask, and thereby calculating the high susceptibility mask.

Similar to the first embodiment, it is also possible to add following processes after the thresholding, i.e., a process for removing an isolated point and a process for setting to zero the high susceptibility region where the area becomes equal to or less than a certain threshold, so as to obtain the high susceptibility mask.

Finally, the low susceptibility mask is calculated (step S1603). In the present embodiment, the high susceptibility mask is subtracted from the high-signal region mask to calculate the low susceptibility mask.

In the present embodiment, the pixel values of the low-signal region mask, of the high susceptibility mask, and of the low susceptibility mask are set to 0 or 1, but any value may be used. For example, a filter processing may be added where a moving-average filter or a similar filter is applied to each of the masks.

[Susceptibility Calculation Process (S1204)]

After creating the three masks as described above, the susceptibility calculation process (step S1204) is performed. According to the susceptibility calculation process in the susceptibility calculator 540, the susceptibility image is calculated, by a method similar to the first embodiment, from the low-signal region mask, the high susceptibility mask, and the low susceptibility mask calculated by the mask calculator 530, and the magnetic field image calculated by the magnetic field calculator 520. In this situation, unlike the first embodiment, the high susceptibility mask may be used instead of the fat mask, and the low susceptibility mask may be used instead of the water mask.

Namely, the background removal processor 841 performs, firstly, the background removal process on the magnetic field image, assuming the region defined by the low-signal region mask as the background region. Then, the susceptibility calculation process is performed on the image where the background has been removed, and under the constraint that the region defined by the low susceptibility mask is set to zero, a susceptibility image (a first susceptibility image) in the region defined by the high susceptibility mask is calculated (a process of the high susceptibility calculator 842). Next, the background removal processor 843 performs a process of removing the background from the magnetic field image, assuming the region defined by the low-signal region mask and the high susceptibility mask as the background regions. Then, the susceptibility calculation process is performed on the image where the background has been removed by the background removal processor 843, and the susceptibility image (the second susceptibility image) of the region defined by the low susceptibility mask is calculated (a process of the low susceptibility calculator 844). Finally, the first susceptibility image and the second susceptibility image are combined so as to calculate a combined susceptibility image (a process of the combined susceptibility calculator 845).

As described so far, in the MRI apparatus of the present embodiment, the mask calculator employs the discriminant susceptibility image calculated with the use of the magnetic field image, to create the high susceptibility region mask associated with the high susceptibility region, and the region mask associated with the high-signal region excluding the high susceptibility region. For the cases such as calculating a brain image with hemorrhage, including two regions whose magnetic susceptibility values are significantly different from each other, and also failing to divide those regions by using the water-fat image, the present embodiment allows reduction of the accuracy degradation due to a signal loss, thereby obtaining a highly accurate susceptibility image.

In the present embodiment, unlike the first embodiment, the mask calculator 530 uses neither the water image nor the fat image, and therefore, the water-fat separation process may not be necessarily performed.

Third Embodiment

In the first and the second embodiments, two high-signal region masks are calculated, and susceptibility images are calculated in the respective regions according to different methods, and finally they are combined to calculate the combined susceptibility image. In the third embodiment, three high-signal region masks are calculated, and susceptibility images are calculated in the respective regions according to different methods, and finally they are combined to calculate a combined susceptibility image. There will now be described the third embodiment, focusing on a configuration that is different from the first embodiment and the second embodiment.

The regions defined respectively by the three high-signal region masks are not limited. For example, those regions may conceivably be a region that may cause high susceptibility such as including hemorrhage, a fat region, and others. The present embodiment will be described, taking such regions as examples in the following.

The MRI apparatus of the present embodiment has basically the same configuration as the first embodiment. Similar to the first embodiment, the computer 209 of the present embodiment, instructs the sequencer 204 to perform measurement of echoes according to measurement parameters and a pulse sequence set via the input device 212 (or provided in advance), measures the echoes, places the obtained echoes in k-space, performs computations on the echoes placed in the k-space to calculate a susceptibility image, and displays an obtained image on the monitor 210.

Figure 14:
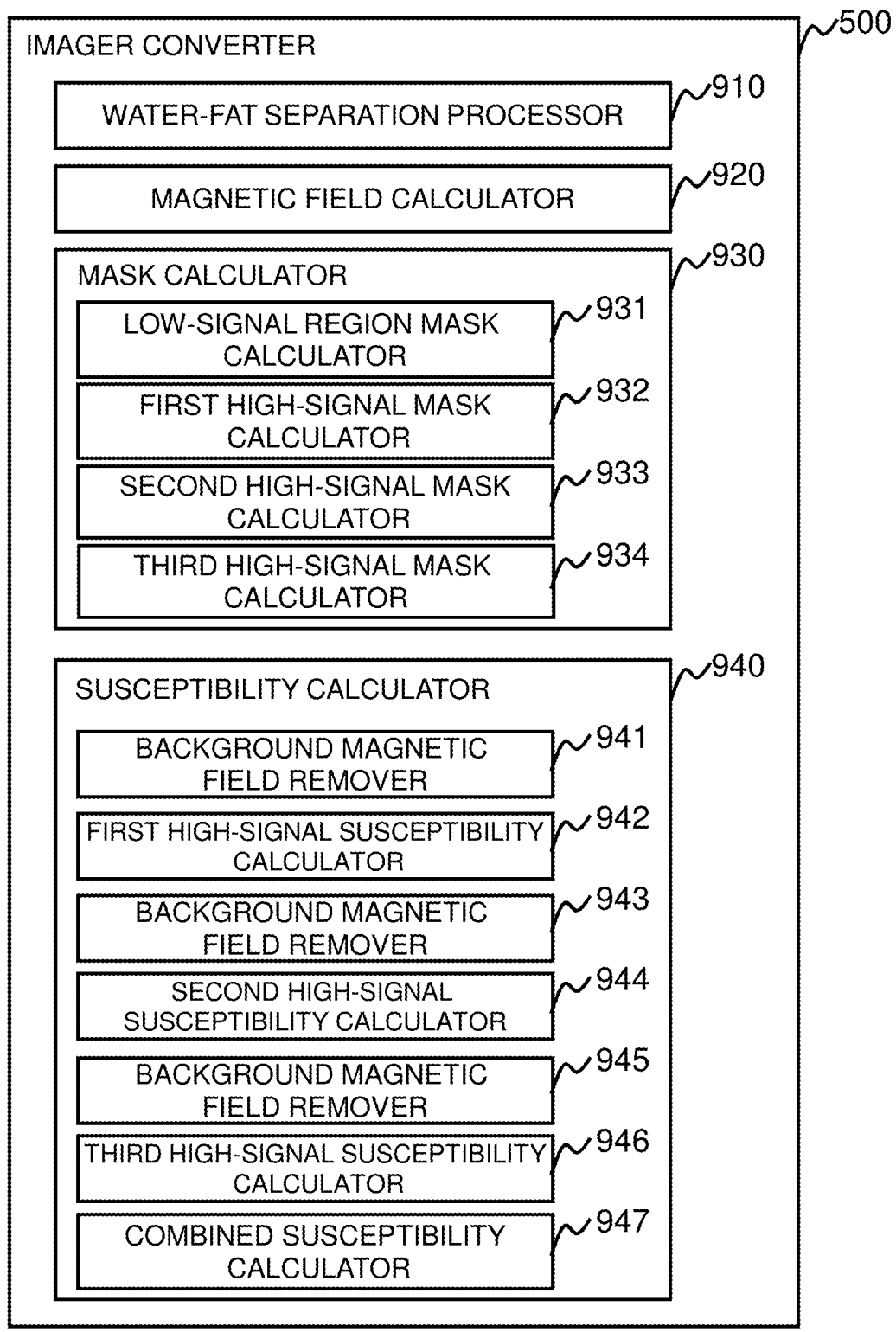
FIG. 14 is a functional block diagram of the image converter according to a third embodiment.

The computer 209 of the present embodiment includes the measurement unit 300, the image reconstructor 400, the image converter 500, and the display processor 600, similar to the first embodiment. FIG. 14 is a functional block diagram showing the image converter 500 of the present embodiment. The image converter 500 of the present embodiment includes a water-fat separation processor 910, a magnetic field calculator 920, a mask calculator 930, and a susceptibility calculator 940, similar to the first embodiment. The mask calculator 930 includes, unlike the first embodiment, a low-signal region mask calculator 931, a first high-signal region mask calculator 932, a second high-signal region mask calculator 933, and a third high-signal region mask calculator 934. The susceptibility calculator 940 includes, unlike the first embodiment, a background magnetic field remover 941, a first high-signal susceptibility calculator 942, a background magnetic field remover 943, a second high-signal susceptibility calculator 944, background magnetic field remover 945, a third high-signal susceptibility calculator 946, and a combined susceptibility calculator 947.

Figure 15:
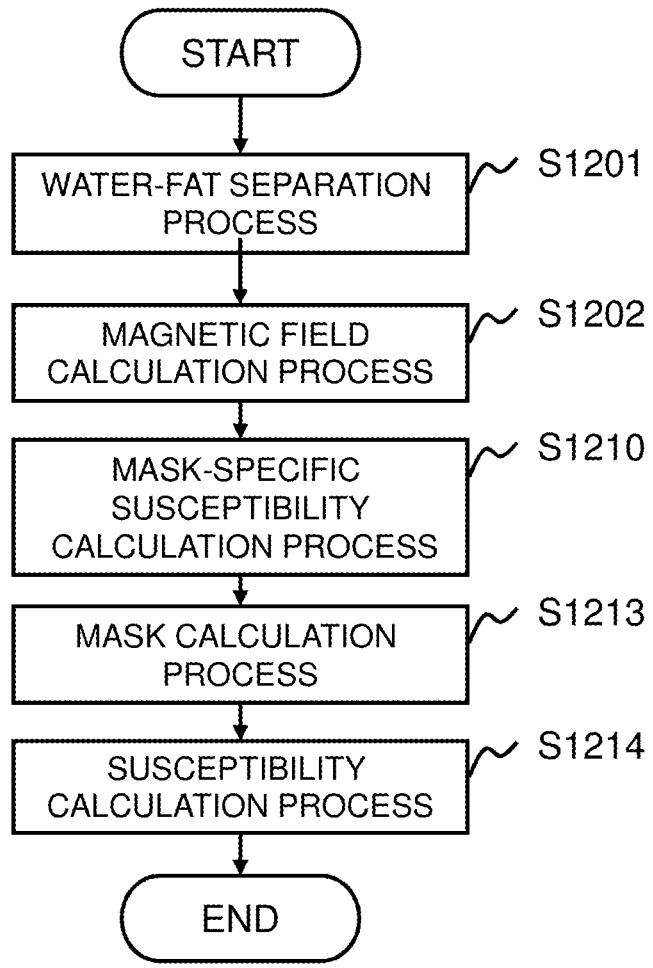
FIG. 15 is a flowchart of the image conversion process according to the third embodiment.

As shown in FIG. 15, the image converter 500 of the present embodiment performs, the water-fat separation process S1201 for calculating a water image, a fat image, a frequency image, and a fat content image, the magnetic field calculation process S1202 for calculating a magnetic field image from the frequency image, a process for calculating a provisional susceptibility image from the magnetic field image (a mask-specific susceptibility image calculation process) S1210, a process for calculating a plurality of region masks (a mask calculation process) S1213, and a process for calculating the susceptibility by using the magnetic field image and the plurality of region masks (a susceptibility calculation process) S1214. In FIG. 15, the processes labeled with the same reference numerals as those in FIG. 6 (the first embodiment) and FIG. 12 (the second embodiment) are performed similarly, and thus redundant descriptions will not be made. There will now be described the mask calculation process S1213 and the susceptibility calculation process S1214.

[Mask Calculation Process (S1213)]

In the mask calculation process S1213, the mask calculator 930 calculates, a low-signal region mask representing a low-signal region such as air, a first high-signal region mask representing a relatively high susceptibility region, a second high-signal region mask representing a fat region, and a third high-signal region mask representing other high-signal regions, from the complex image calculated in the image reconstructor 400, the fat content image calculated in the water-fat separation processor 910, and the magnetic field image calculated in the magnetic field calculator 920.

Figure 16:
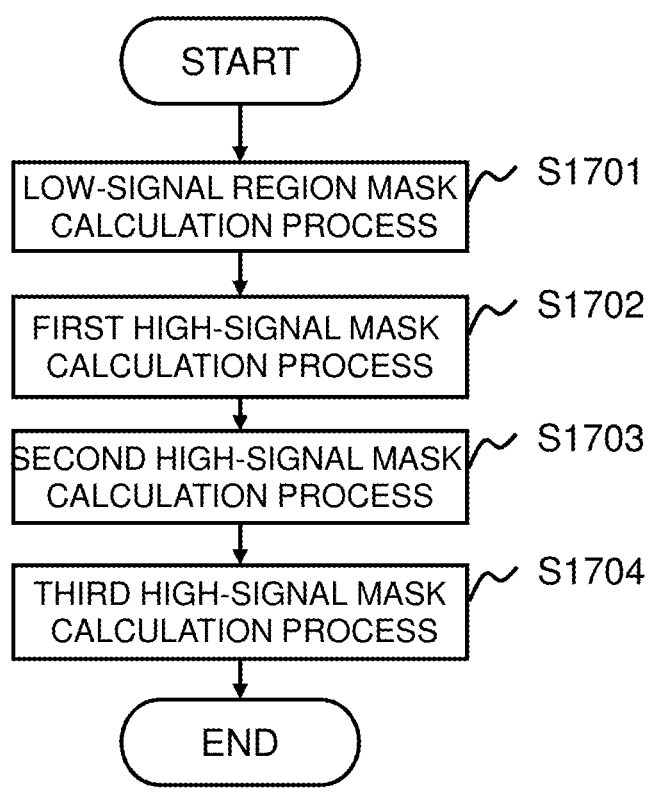
FIG. 16 is a flowchart of the mask calculation process according to the third embodiment.
Figure 17:
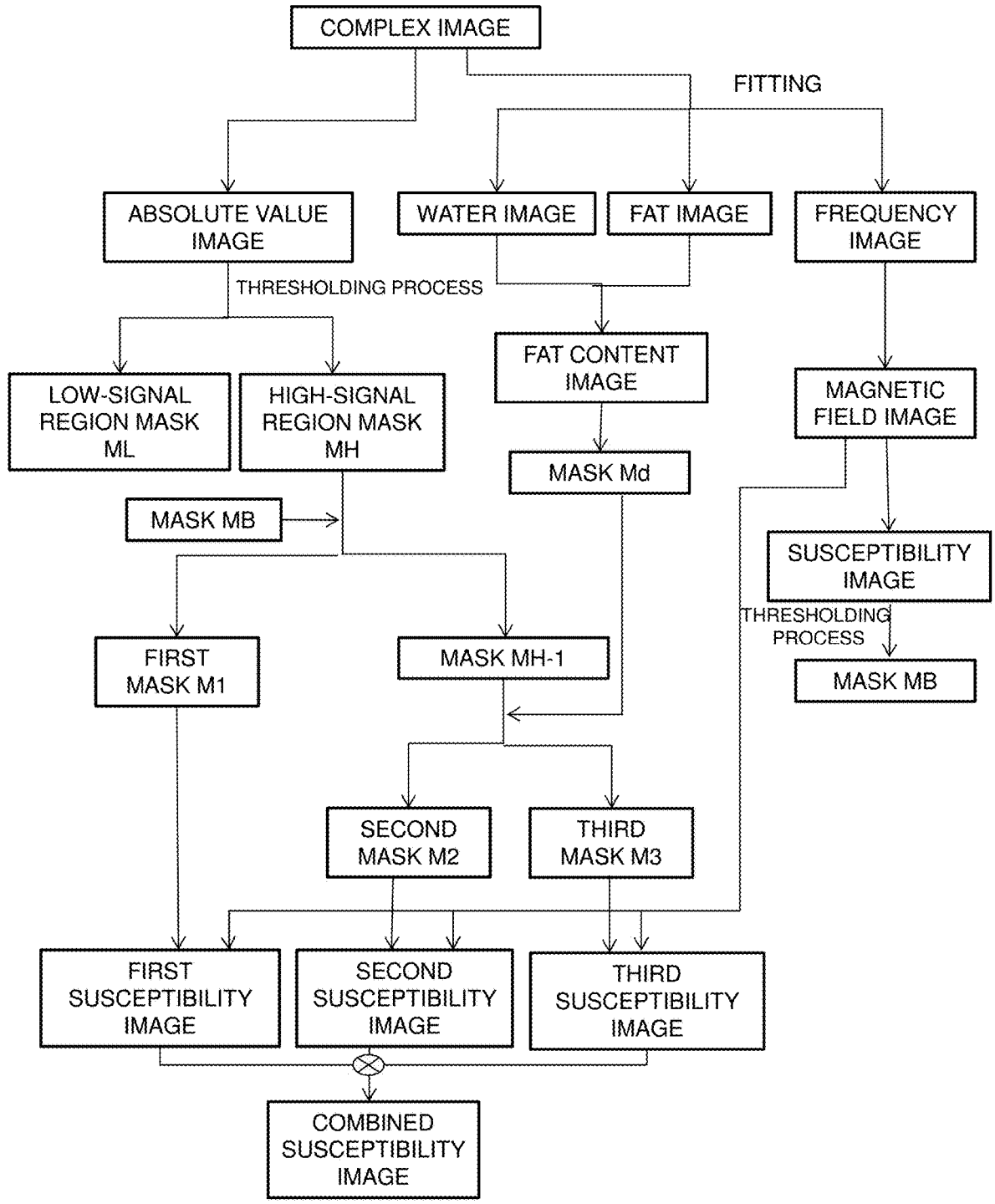
FIG. 17 illustrates a relationship between images and masks, used in calculating the masks and in calculating the susceptibility according to the third embodiment.

FIG. 16 is a flowchart showing the mask calculation process of the present embodiment, and FIG. 17 illustrates a relationship between the images used for mask calculation and the masks being calculated. In the mask calculation process, firstly, a low-signal region mask $M_L$ and a high-signal region mask $M_H$ are calculated (step S1701). Next, the first high-signal region mask $M_1$ is calculated from the high-signal region mask $M_H$ and the mask-specific susceptibility image (step S1702). Then, the second high-signal region mask $M_2$ is calculated from the high-signal region mask $M_H$, the first high-signal region mask $M_1$, and the fat content image (step S1703). Finally, the third high-signal region mask $M_3$ is calculated from the high-signal region mask $M_H$, the first high-signal region mask $M_1$, and the second high-signal region mask $M_2$ (step S1704). There will now be described details of each of the processes.

The low-signal region mask calculation method of the step S1701 is basically the same as the first embodiment, and a mask-specific absolute value image is calculated from the complex image, thresholding is performed on the mask-specific absolute value image, and the low-signal region mask $M_L$ and the high-signal region mask $M_H$ are calculated (a process of the low-signal region mask calculator 931).

Next, in step S1702, according to a method similar to the high susceptibility mask calculation method of the second embodiment, the mask-specific susceptibility image calculated in step S1210 is used as a discriminant image, and thresholding is performed using a certain threshold, thereby calculating the mask (the first high-signal region mask) $M_1$ (a process of the first high-signal mask calculator 932).

Next, the second high-signal region mask $M_2$ is calculated in step S1703. For this purpose, firstly, thresholding is performed on the fat content image calculated in the water-fat separation process S1201, by using a certain threshold, thereby calculating the mask Md. For example, the region where the fat content is higher than the threshold is set to 1, and the region where the fat content is equal to or lower than the threshold is set to zero. In the present embodiment, the threshold is set to 0.8. Then, the mask Md calculated according to the thresholding is multiplied by the mask $M_{(H-1)}$ that is obtained by subtracting the first high-signal region mask $M_1$ from the high-signal region mask $M_H$, thereby calculating the second high-signal region mask $M_2$.

Finally, the third high-signal region mask $M_3$ is calculated by subtracting the first high-signal region mask $M_1$ and the second high-signal region mask $M_2$, from the high-signal region mask MH (step S1704).

In the present embodiment, the calculated four masks take the values 0 and 1 only, but they may be any values, similar to the first embodiment and the second embodiment. Furthermore, similar to the first embodiment and the second embodiment, an additional process such as the isolated point removal process may be performed on each of thus calculated masks.

[Susceptibility Calculation Process (S1214)]

Next, a processing flow of the susceptibility calculation S1214 of the present embodiment will be described. The susceptibility calculator 940 calculates the susceptibility images, from the low-signal region mask $M_L$, the first high-signal region mask $M_1$, the second high-signal region mask $M_2$, and the third high-signal region mask $M_3$, which are calculated in the mask calculator 930, and the magnetic field image calculated by the magnetic field calculator 920.

Figure 18:
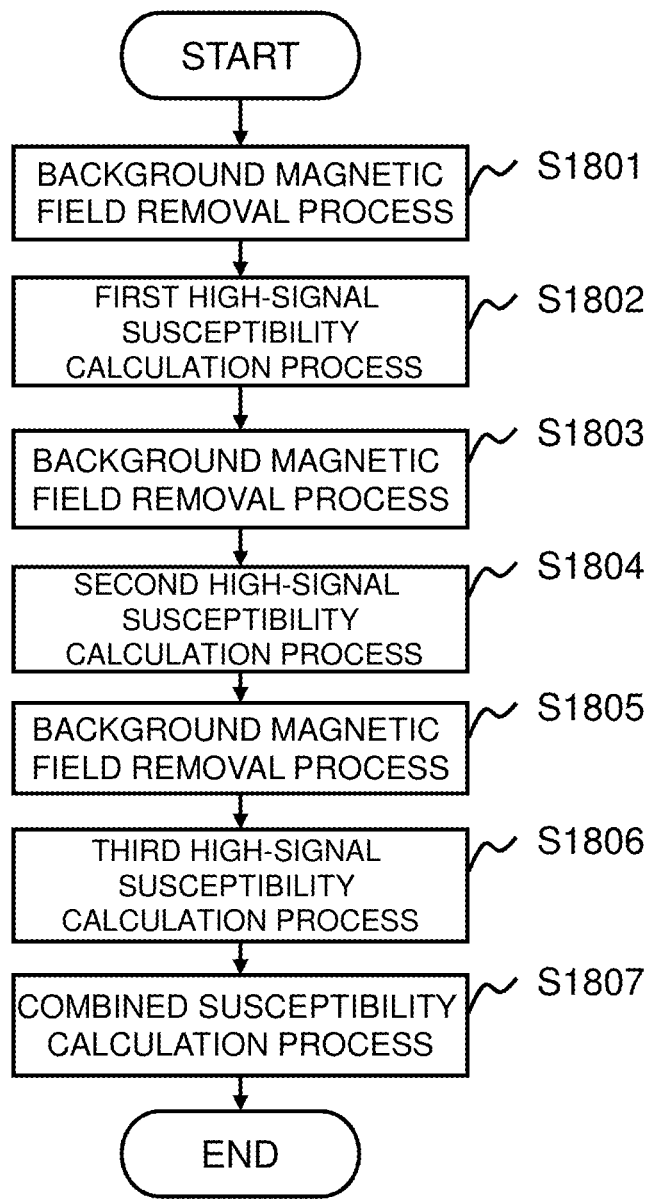
FIG. 18 is a flowchart of the susceptibility calculation process according to the third embodiment.

FIG. 18 is a flowchart of the susceptibility calculation process of the present embodiment. In the present embodiment, the background removal process is performed on the magnetic field image, assuming the region defined by the low-signal region mask as the background region (step S1801). Next, the susceptibility calculation process is performed on the magnetic field image where the background has been removed in step S1801, and the first high-signal susceptibility image is calculated, under the constraint that the susceptibility of the region defined by the sum of the second high-signal region mask $M_2$ and the third high-signal region mask $M_3$ is assumed as zero (step S1802). Next, the background removal process is performed on the magnetic field image, assuming the region defined by the low-signal region mask $M_L$ and the first high-signal region mask $M_1$ as the background (step S1803). Then, from the magnetic field image where the background has been removed in step S1803, the second high-signal susceptibility image is calculated under the constraint that the third high-signal region mask $M_3$ is zero (step S1804). Next, the background removal process is performed, assuming as the background, the region defined by the low-signal region mask $M_L$, the first high-signal region mask $M_1$ and the second high-signal region mask $M_2$ (step S1805). Next, the susceptibility image is calculated from the image where the background has been removed in step S1805 (step S1806).

The background magnetic field removing method in each of steps S1801, S1803, and S1805 is basically the same as the method described in the first embodiment, except the point that the background region is different. The method for calculating the susceptibility image in each of steps S1802 and S1804 under the constraint that the susceptibility of a partial region is assumed as zero, is basically the same as the method described in the first embodiment, except the point that the region of interest and the region where the constraint is placed are different. The method of calculating the susceptibility image in step S1806 is basically the same as the method of S1504 of the first embodiment, except the point that the region of interest is different.

Finally, according to the following formula 22, the first high-signal susceptibility image, the second high-signal susceptibility image, and the third high-signal susceptibility image are combined, thereby calculating the combined susceptibility image $\chi$ (step S1807).

[Formula 22]

$$\chi = M_1\chi_1 + M_2\chi_2 + M_3\chi_3 \quad (22)$$

where $M_1$, $M_2$, and $M_3$ are respectively the first high-signal region mask, the second high-signal region mask, and the third high-signal region mask, $\chi_1$, $\chi_2$, and $\chi_3$ are respectively the first high-signal susceptibility image, the second high-signal susceptibility image, and the third-signal susceptibility image.

In the MRI apparatus of the present embodiment, the image converter is further provided with the water-fat separator that uses an image created by the image reconstructor, for separating a water image where signals from water protons are dominant and a fat image where signals from fat protons are dominant, among the substances contained in the subject, and the mask calculator uses the fat content calculated as to each pixel using the water image and the fat image, and a discriminant susceptibility image calculated from the magnetic field image, so as to create a high susceptibility region mask associated with the high susceptibility region, a fat mask associated with the region where fat is dominant, and a region mask associated with a region excluding the regions defined by the high susceptibility region mask and the fat mask.

According to the present embodiment, when the image includes three regions where the susceptibility is significantly different, such as a hemorrhage region, fat region, and other regions, the accuracy degradation due to the signal loss may be reduced, thereby calculating a highly accurate susceptibility image.

The number of regions is not limited to three, and the present processing may be similarly applied to four or more regions. It is also possible to use two thresholds for thresholding the mask-specific susceptibility image, in order to calculate three high-signal region masks.

EXAMPLE

Example of the First Embodiment

As shown in the following table 1, assuming a model where the susceptibility inside the fat was 0.61, the susceptibility outside the fat was 0, and the susceptibility images were obtained by simulation from the model, according to the susceptibility calculation method (the method of the present invention) of the first embodiment and a conventional method. As the conventional method, there was employed a method for calculating the susceptibility under the constraint that the susceptibility of the high-signal region was smoothed after removing the background being the low-signal region.

Figure 19:
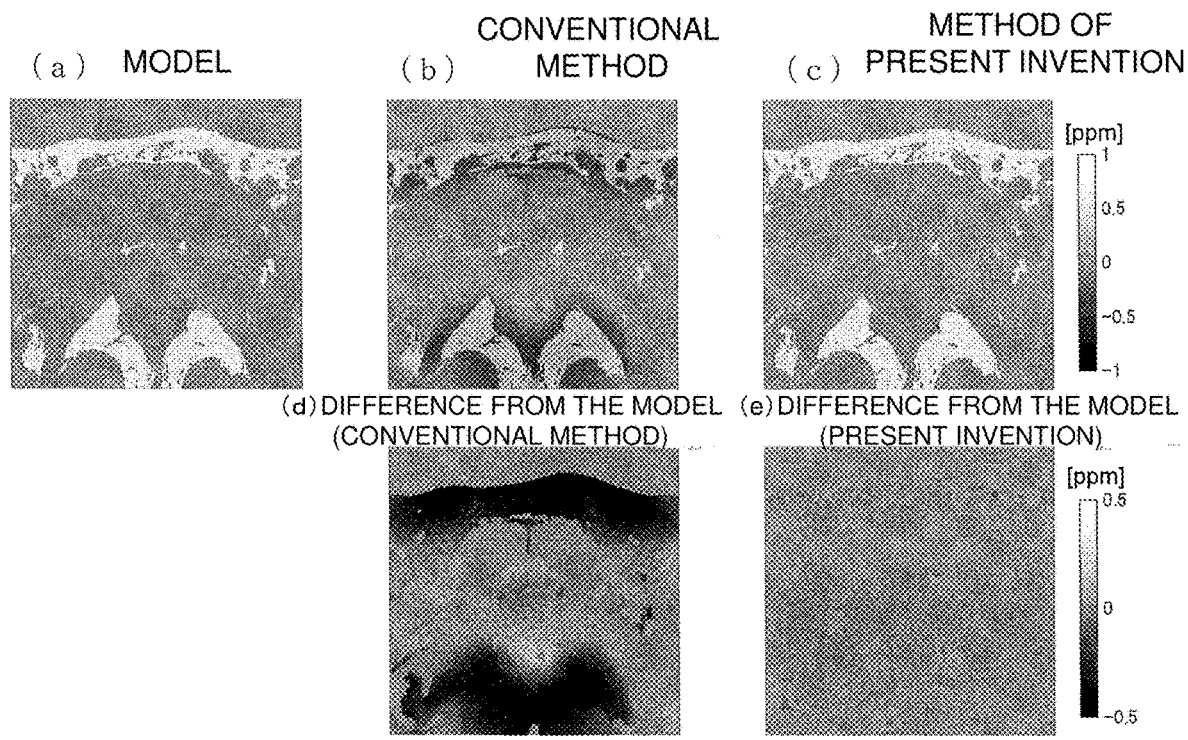
FIGS. 19(a) to 19(e) illustrate results of examples.

Table 1 and FIG. 19 show results of the simulation. FIGS. 19(a), 19(b), and 19(c) respectively show the susceptibility images of the model, the conventional method, and the method of the present invention, FIGS. 19(d) and 19(e) show a difference between the model and the susceptibility image, where FIG. 19(d) depicts the difference when the conventional method was used and FIG. 19(e) depicts the difference when the method of the present invention was used.

TABLE 1

| | AVERAGE SUSCEPTIBILITY [ppm] | | ERROR RMSE [ppm] | |
|---|---|---|---|---|
| | INSIDE THE FAT | OUTSIDE THE FAT | INSIDE THE FAT | OUTSIDE THE FAT |
| CONVENTIONAL METHOD | 0.299 | −0.052 | 0.330 | 0.129 |
| PRESENT INVENTION | 0.606 | 0.000 | 0.047 | 0.036 |
| MODEL | 0.61 | 0 | — | — |

RMSE (Root Mean Square Error): Mean Square Error

According to the results of the simulation, it was confirmed that with the method of the present invention, errors was drastically reduced, and accuracy of the susceptibility calculation was enhanced.

DESCRIPTION OF SYMBOLS

100: vertical field MRI apparatus, 101: horizontal field MRI apparatus, 102: MRI apparatus, 201: magnet, 202: gradient coil, 203: subject, 204: sequencer, 205: gradient magnetic field power supply, 206: RF magnetic field generator, 207: probe, 208: receiver, 209: computer, 210: monitor, 211: storage device, 212: input device, 300: measurement unit, 400: image reconstructor, 500: image converter, 510: water-fat separation processor, 520: magnetic field calculator, 530: mask calculator, 531: mask calculator for low-signal region, 532: mask calculator for fat, 533: mask calculator for water, 540: susceptibility calculator, 541: background magnetic field remover, 542: fat susceptibility calculator, 543: background magnetic field remover, 544: water susceptibility calculator, 545: combined susceptibility calculator, 550: mask-specific susceptibility calculator, 600: display processor, 710: GrE-type pulse sequence, 711: RF pulse, 712: slice selective gradient magnetic field, 713: phase encoding gradient magnetic field, 721: readout gradient magnetic field, 722: readout gradient magnetic field, 723: readout gradient magnetic field, 724: readout gradient magnetic field, 731: first echo signal, 732: second echo signal, 733: third echo signal, 734: fourth echo signal, 810: mask calculator for low-signal region, 820: high susceptibility mask calculator, 830: low susceptibility mask calculator, 910: water-fat separation processor, 920: magnetic field calculator, 930: mask calculator, 940: susceptibility calculator

What is claimed is:

1. A magnetic resonance imaging apparatus, comprising,
a static magnetic field magnet,
a magnetic field generator configured to apply a gradient magnetic field and an RF magnetic field to space formed by the static magnetic field magnet,
a receiver configured to receive a nuclear magnetic resonance signal generated from a subject placed in the space, and
a computer configured to perform computations on the nuclear magnetic resonance signal,
wherein the computer is configured to execute:
a measurement unit configured to control the magnetic field generator and the receiver, and to measure the nuclear magnetic resonance signal including effects of magnetic field inhomogeneity,
an image reconstructor configured to perform image reconstruction by using the nuclear magnetic resonance signal, so as to create a complex image, and
an image converter configured to calculate a susceptibility image of the subject, by using the complex image,
a magnetic field calculator configured to calculate a magnetic field reflected image from the complex image,
a mask calculator configured to use the complex image created by the image reconstructor to calculate a low-signal region mask associated with a low-signal region, and a plurality of region masks associated with a plurality of regions in a high-signal region, and
a susceptibility calculator configured to use the magnetic field reflected image calculated by the magnetic field calculator, the low-signal region mask and the plurality of region masks calculated by the mask calculator, and to calculate susceptibility as to each of the plurality of regions to generate the susceptibility image, and
wherein the susceptibility calculator calculates the susceptibility of a region different from a specific region, under a first constraint that the low-signal region is set as a background, and a second constraint that the susceptibility of the specific region among the plurality of the regions is set to a specific value.

2. The magnetic resonance imaging apparatus, according to claim 1, wherein,
the susceptibility calculator calculates the susceptibility of the specific region, under a third constraint that the low-signal region and the region different from the specific region are set as the background, and combines thus calculated susceptibility of the specific region and the susceptibility of the region different from the specific region.

3. The magnetic resonance imaging apparatus according to claim 2, wherein,
the image converter further comprises a water-fat separator that uses the image created by the image reconstructor, to separate a water image where signals from water protons are dominant, and a fat image where signals from fat protons are dominant, among the substances contained in the subject, and the mask calculator uses a fat content calculated as to each pixel using the water image and the fat image, and a discriminant susceptibility image calculated using the magnetic field reflected image, so as to create a high susceptibility region mask associated with a high susceptibility region, a fat mask associated with the region where fat is dominant, and a region mask associated with a region excluding the regions defined by the high susceptibility region mask and the fat mask.

4. The magnetic resonance imaging apparatus, according to claim 1,
wherein the computer is configured to execute:
a water-fat separator configured to use the image created by the image reconstructor to separate a water image where signals from water protons are dominant, and a fat image where signals from fat protons are dominant, and
wherein the mask calculator uses a predetermined value of a fat content as to each pixel, calculated by using the water image and the fat image, to create the plurality of region masks, including a water mask associated with a region where water is dominant, and a fat mask associated with a region where fat is dominant.

5. The magnetic resonance imaging apparatus, according to claim 4, wherein,
the specific region is the region where water is dominant and the specific value is zero, in the calculation by the susceptibility calculator.

6. The magnetic resonance imaging apparatus, according to claim 4, wherein,
the specific region is the region where fat is dominant and the specific value is a predetermined positive constant, in the calculation by the susceptibility calculator.

7. The magnetic resonance imaging apparatus, according to claim 4, wherein,
the measurement unit measures a plurality of nuclear magnetic resonance signals, at least three, at different echo times, and
the water-fat separator calculates the water image, the fat image, and a frequency image representing a frequency distribution of the subject, according to fitting of the plurality of nuclear magnetic resonance signals at different echo times to signal models.

8. The magnetic resonance imaging apparatus according to claim 7, wherein,
the magnetic field calculator calculates the magnetic field reflected image, from the frequency image calculated by the water-fat separator.

9. The magnetic resonance imaging apparatus according to claim 1, wherein,
the mask calculator uses a discriminant susceptibility image calculated by using the magnetic field reflected image, to calculate a high susceptibility region mask associated with a high susceptibility region, and a region mask associated with the high-signal region excluding the high susceptibility region.

10. A magnetic resonance imaging method, comprising,
measuring a nuclear magnetic resonance signal including effects of magnetic field inhomogeneity,
creating a complex image by using the nuclear magnetic resonance signal, and
creating a magnetic field reflected image by using the complex image, and creating a susceptibility image by using the magnetic field reflected image,
wherein a low-signal region mask and a high-signal mask are generated by using an absolute value image created from the complex image, and a first region mask and a second region mask are created from the high-signal mask, the first region mask representing a first region where a pixel value of a certain discriminant image is larger than a predetermined threshold and the second region mask representing a second region where the pixel value of the discriminant image is equal to or smaller than the predetermined threshold, and wherein by using the magnetic field reflected image, the low-signal region mask, and the first and the second region masks, a first region susceptibility image is calculated under a first constraint that a region defined by the low-signal region mask is set as a background, and a second constraint that the susceptibility of the second region is set to a specific value, and a second region susceptibility image is calculated under the constraint that the region defined by the low-signal region mask and the first region are set as the background.

11. The magnetic resonance imaging method according to claim 10, wherein, calculating the susceptibility of the first region further includes a third constraint that the susceptibility is smoothed.

12. The magnetic resonance imaging method according to claim 11, wherein, in calculating the susceptibility, a parameter value representing strength of the first constraint for setting the specific value, and a parameter value representing strength of the third constraint for smoothing are set to values that are obtained when a mean value and a standard deviation of the susceptibility in the region defined by the first region mask are maximized.

13. The magnetic resonance imaging method according to claim 10, wherein, the plurality of region masks include a water mask associated with a region where signals from water protons are dominant, and a fat mask associated with a region where signals from fat protons are dominant, and the specific value of the region defined by the water mask is set to zero in calculating the susceptibility.

14. The magnetic resonance imaging method according to claim 13, further comprising, creating a water image of the region where water is dominant and a fat image of the region where fat is dominant, by using the complex image, calculating a fat content as to each pixel, by using the water image and the fat image, and dividing the high-signal mask into the first region mask and the second region mask, using as a threshold, a predetermined value of the fat content as to each pixel.

15. A non-transitory computer readable medium storing a susceptibility calculation program causing a computer to execute steps comprising:

creating a complex image using a nuclear magnetic resonance signal including effects of magnetic field inhomogeneity, measured by a magnetic resonance imaging apparatus, creating a magnetic field reflected image by using the complex image, creating an absolute value image from the complex image, creating a low-signal region mask and a high-signal mask by using the absolute value image, and further creating from the high-signal mask, a plurality of region masks associated with a plurality of regions, calculating the first susceptibility of a region excluding a specific region, by using the magnetic field reflected image, the low-signal region mask, and the plurality of region masks, under a first constraint that a region defined by the low-signal mask is set as a background, and a second constraint that the susceptibility of the specific region among the plurality of regions is set to a specific value, calculating the second susceptibility of the specific region, under a third constraint for setting as the background, the region defined by the low-signal region mask and the region defined by the region mask associated with a region excluding the specific region, and combining the first susceptibility and the second susceptibility to generate a susceptibility image.

* * * * *